US011427574B2

(12) United States Patent
Williams et al.

(10) Patent No.: US 11,427,574 B2
(45) Date of Patent: *Aug. 30, 2022

(54) COMPOUNDS FOR TREATING RAC-GTPASE MEDIATED DISORDER

(71) Applicant: Children's Medical Center Corporation, Boston, MA (US)

(72) Inventors: David A Williams, Dover, MA (US); Serena De Vita, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/920,016

(22) Filed: Jul. 2, 2020

(65) Prior Publication Data
US 2020/0331901 A1    Oct. 22, 2020

Related U.S. Application Data

(63) Continuation of application No. 15/567,302, filed as application No. PCT/US2016/027715 on Apr. 15, 2016, now Pat. No. 10,774,075.

(60) Provisional application No. 62/152,350, filed on Apr. 24, 2015.

(51) Int. Cl.
| | | |
|---|---|---|
| C07D 413/06 | (2006.01) | |
| C07D 413/14 | (2006.01) | |
| A61K 31/4439 | (2006.01) | |
| A61K 31/4245 | (2006.01) | |
| A61P 35/02 | (2006.01) | |
| A61P 19/08 | (2006.01) | |
| A61P 29/00 | (2006.01) | |
| A61K 45/06 | (2006.01) | |

(52) U.S. Cl.
CPC ........ *C07D 413/14* (2013.01); *A61K 31/4245* (2013.01); *A61K 31/4439* (2013.01); *A61K 45/06* (2013.01); *A61P 19/08* (2018.01); *A61P 29/00* (2018.01); *A61P 35/02* (2018.01); *C07D 413/06* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 2002/0155166 A1 | 10/2002 | Choi et al. |
| 2008/0139538 A1 | 6/2008 | McGaughey et al. |
| 2009/0325956 A1 | 12/2009 | Taniguchi et al. |
| 2010/0120810 A1 | 5/2010 | Leblond et al. |
| 2010/0197703 A1 | 8/2010 | Griffioen et al. |
| 2011/0021509 A1 | 1/2011 | Bergmann et al. |
| 2012/0253040 A1 | 10/2012 | Masuda et al. |

FOREIGN PATENT DOCUMENTS

| | | |
|---|---|---|
| WO | WO 2014059305 | 4/2004 |
| WO | WO 2008086854 | 7/2008 |
| WO | WO 2010096830 | 8/2010 |
| WO | WO 2010119050 | 10/2010 |
| WO | WO 2012119941 | 9/2012 |
| WO | WO 2016172001 | 10/2016 |

OTHER PUBLICATIONS

CAS RN 1070331-22-4 (entered into STN on Nov. 3, 2008) (Year: 2008).*
CAS RN 1069615-20-8 (entered into STN on Nov. 2, 2008) (Year: 2008).*
Ito et al (Cancer Science 94:3-8, 2003) (Year: 2003).*
CN Office Action in Chinese Appln No. 201680035893.0, dated Jul. 8, 2020, 11 pages (with English translation).
[No Author], RN: 10695222-36-6, Chemical Library, 2020, 1 pages.
AU Office Action in Australian Appln. No. 2016252029, dated Oct. 17, 2019, 3 pages.
Boettner and Van Aelst, "The role of Rho GTPases in disease development," Gene, Mar. 2002, 286: 155-174.
CAS RN 1069615-20-8, dated Nov. 2, 2008, 2 pages.
Database Accession No. 1069677-48-0, Chemical Abstracts Service, Nov. 2008, 5 pages.
Etienne-Manneville and Hall, "Rho GTPases in cell biology," Nature, Dec. 2002, 420: 629-635.
European Search Report in Application No. 16783626.1, dated Aug. 16, 2018, 6 pages.
European Search Report; EP 13845005.1; dated Apr. 16, 2008; 7 pp.
Ferraro et al., "Pro-metastatic signaling by c-Met through RAC-1 and reactive oxygen species (ROS)," Oncogene, 2006, 25: 3689-3698).
Gao et al., "Rational design and characterization of a Rac GTPase-specific small molecule inhibitor," PNAS, 2004, 101: 7618-7623.
Gerard et al., "Synthesis of a stereochemically diverse library of medium-sized lactams and sultams via S(N)Ar cycloetherification," ACS Comb. Sci, 2011, 13: 365-374.
Hall, "Rho GTPases and the Actin Cytoskeleton," Science, 1998, 279: 509-514.
Hwang et al., "Expression of Rac3 in human brain tumors," J. Clin. Neurosci, Jun. 2005, 12: 571-574).
International Preliminary Report on Patentability in International Application No. PCT/US2016/027715, dated Nov. 2, 2017, 9 pages.
International Search Report and Written Opinion in International Application No. PCT/US2016/027715, dated Sep. 2, 2016, 15 pages.
International Search Report and Written Opinion issued in PCT/US2013/064590 dated Feb. 12, 2014 (14 pages).
Ito et al., "A medium-term rat liver bioassay for rapid in vivo detection of carcinogenic potential of chemicals," Cancer Science, Nov. 18, 2002, 94:3-8.

(Continued)

*Primary Examiner* — Craig D Ricci
(74) *Attorney, Agent, or Firm* — Fish & Richardson P.C.

(57) ABSTRACT

This disclosure relates to compositions including certain compounds identified by a quantitative, high throughput assay to be effective in the treatment of a Rac-GTPase mediated disorder (e.g., acute lymphoblastic or chronic myelogenous leukemia), as well as methods for the manufacture of and the use of these compounds for treating a Rac-GTPase mediated disorder.

6 Claims, 14 Drawing Sheets

(56) References Cited

OTHER PUBLICATIONS

JP Office Action in Japanese Appln. No. 2017-555546, dated Feb. 10, 2020, 8 pages (With English Translation).
Karnoub et al., "Molecular Basis for Rho GTPase Signaling Specificity," Breast Cancer Res. Treat, Mar. 2004, 84: 61-71.
Khosravi-Far et al., Mol. Cell. Biol, 1995, 15: 6443-6453.
Malumbres and Barbacid, "RAS oncogenes: the first 30 years," Nat. Rev. Cancer, 2003, 3: 459-465.
Mizukawa et al., "Inhibition of Rac GTPase signaling and downstream prosurvival Bcl-2 proteins as combination targeted therapy in MLL-AF9 leukemia," Blood, Nov. 2011, 118:5235-45.
Murray et al., "Small-molecule p21-activated kinase inhibitor PF-3758309 is a potent inhibitor of oncogenic signaling and tumor growth," PNAS, May 2010, 107: 9446-9451.
Pub Chem CID_25490623, dated May 27, 2009, retrieved on May 1, 2016, http://pubchem.ncbi.nlm.nih.gov/compound/25490623, 10 pages.
Qiu et al., "An essential role for Rac in Ras transformation," Nature, Mar. 1995, 374: 457-459.
Renshaw et al., "Rac is required for v-Abl tyrosine kinase to activate mitogenesis," Curr. Biol, 1996, 6: 76-83.
Ridley, "Rho GTPases and actin dynamics in membrane protrusions and vesicle trafficking," Trends Cell Biol, 2006, 16: 522-529.
RN 1069615-20-8, Registry [online], Nov. 2, 2008, [search on Jan. 23, 2019], Retrieved from:STN, 1 page.
Thomas et al., "Rac GTPases as key regulators of p210-BCR-ABL-dependent leukemogenesis," Leukemia, May 2008, 22: 898-904.
USPTO Final Office Action in U.S. Appl. No. 15/567,302, dated Nov. 22, 2019, 7 pages.
Wagner et al., "Synthesis and pharmacological screening of derivatives of isoxazolo[ 4,5-d]pyrimidine," European Journal of Medicinal Chemistiy, 2008, 43: 2498-2504.
Wennerberg and Der, "Rho-family GTPases: it's not only Rac and Rho (and I like it)," J. Cell Sci, 2004, 117: 1301-1312.
Wemuth edited, translated by Nagase Hiroyuki, latest drug chemistry, 1998, pp. 353 to 367, English copy available as The Practice of Medicinal Chemistry, 1st Ed, Academic Press, 1996, pp. 311-324, 30 pages.
Williams et al (Foye's Principles of Medicinal Chemistry, 5th Ed., pp. 59-63, 2002) (Year: 2002).
Office Action in Chinese Appln. No. 201680035893, dated Mar. 24. 2021, 13 pages (with English translation).
CN Office Action in Chinese Appln. No. 201680035893.0, dated Jan. 6, 2021, 12 pages (with English translation).

\* cited by examiner

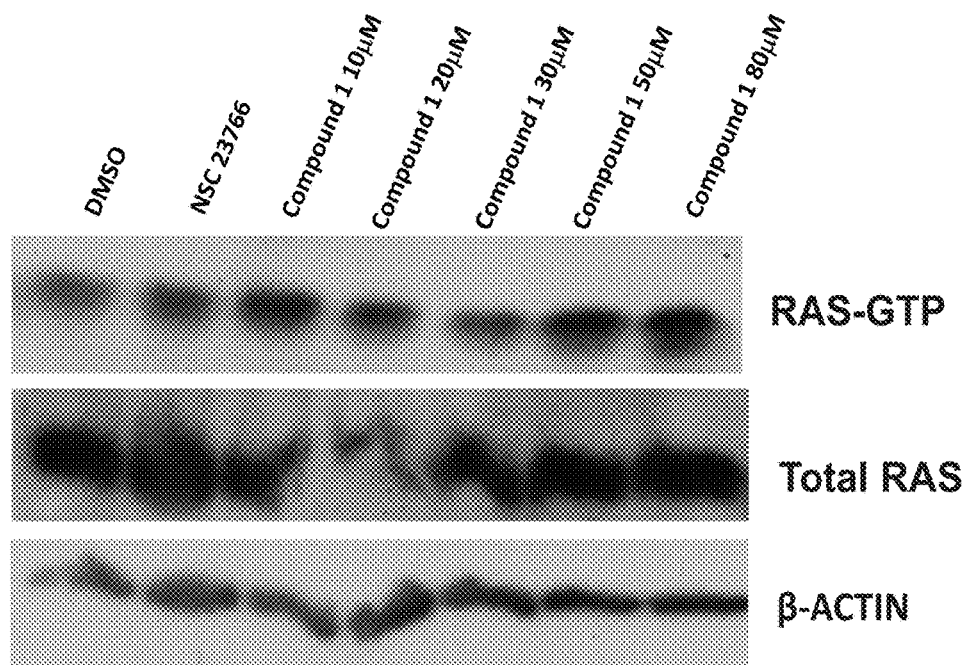
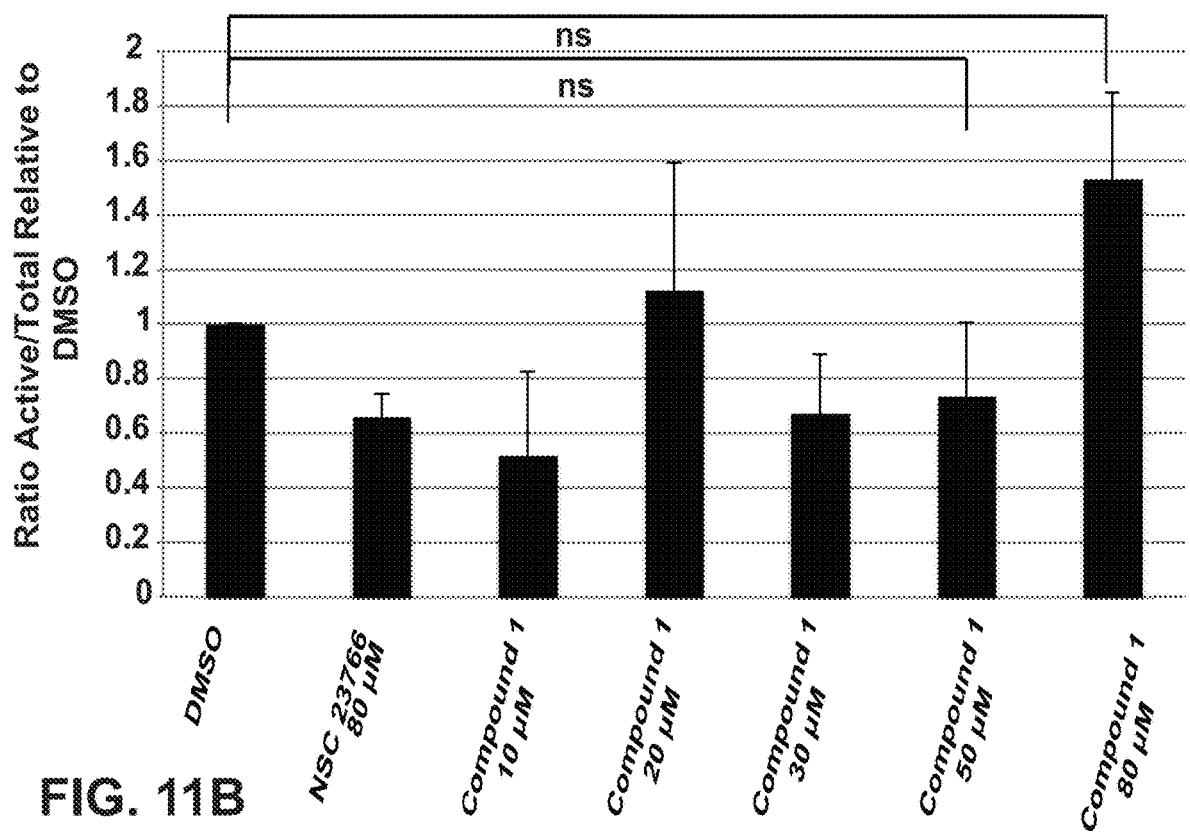
FIG. 11B

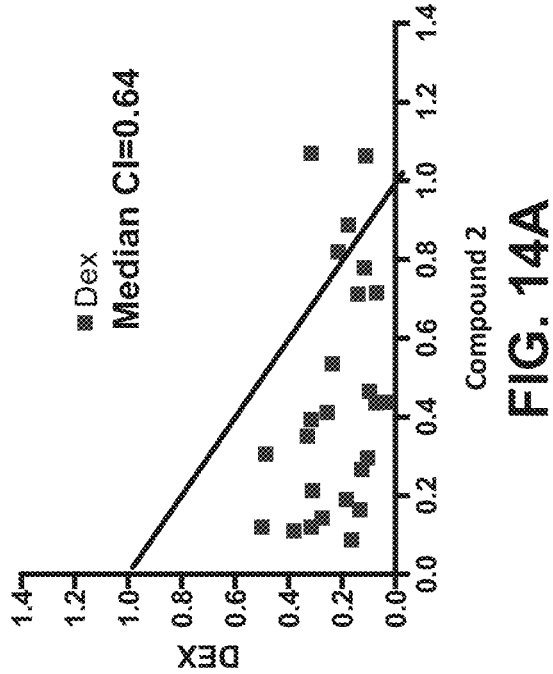
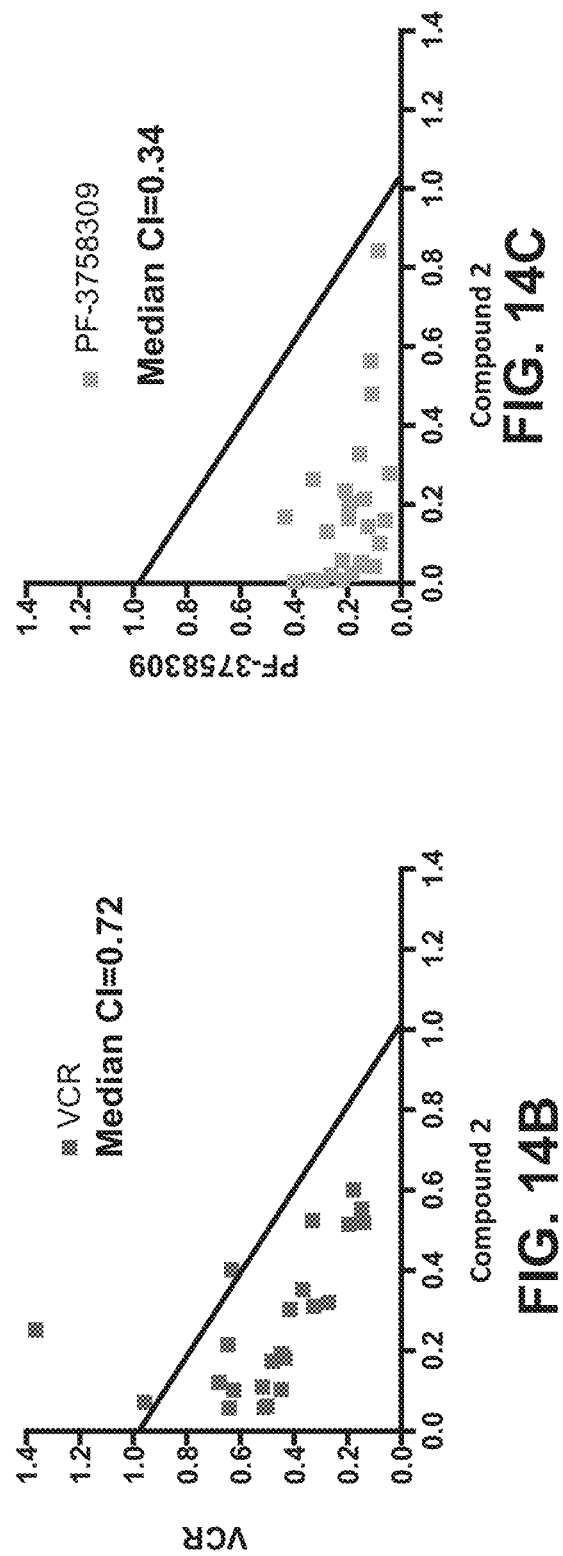

COMPOUNDS FOR TREATING RAC-GTPASE MEDIATED DISORDER

CROSS-REFERENCE TO RELATED APPLICATIONS

This application is a continuation of U.S. application Ser. No. 15/567,302, filed on Oct. 17, 2017, which is a 371 U.S. National Phase Application of International Application No. PCT/US2016/027715, filed on Apr. 15, 2016, which claims priority under 35 U.S.C. § 119(e) to U.S. Provisional Application No. 62/152,350, filed on Apr. 24, 2015. The contents of the parent applications are incorporated herein in their entirety.

BACKGROUND

Rho GTPases comprise a branch of the Ras superfamily of small GTPases. They play a key role in the modulation of a wide array of cellular processes including cell migration, cell polarization, membrane trafficking, cytoskeleton arrangements, proliferation, apoptosis, and transcriptional regulation. (Etienne-Manneville, S. et al (2002). Nature 420, 629-635; Boettner, B. et al. (2002). Gene 286, 155-174.) Hence, Rho GTPases have been implicated in the pathogenesis of various human diseases including cardiovascular diseases and cancer (Hall, A. Science 1998, 279, 509-514; Wennerberg, K., and Der, C. J. (2004) J. Cell Sci. 117, 1301-1312; Ridley, A. J. (2006) Trends Cell Biol. 16, 522-529).

The Rho family is comprised of 22 genes encoding at least 25 proteins in humans including Rac. Rho family members bind GTP and transition between an inactive GDP-bound and an active GTP-bound state. In doing so, many of the Rho family members exhibit a GTPase activity when in their active state. This cycling between states is regulated by: guanine nucleotide exchange factors (GEFs); the GTPase activating proteins (GAPs); and GDP dissociation inhibitors (GDIs) which act as negative regulators. (Malumbres, M. et al (2003) Nat. Rev. Cancer 3, 459-465). In quiescent cells, Rho GTPases are predominantly present in an inactive GDP bound state whereas upon growth stimulation, GEFs are activated and subsequently stimulate the guanine nucleotide exchange activity to promote formation of the active GTP bound Rho. When bound to GTP, active Rho GTPases interact with downstream effectors including protein kinases and other proteins with adaptor functions. The intrinsic GTP hydrolysis functionality of Rho GTPases is later stimulated by the Rho specific GTPase activating protein. This returns the Rho protein to its inactive state. Rac-specific RhoGEFs include Tiam1 and Trio (Gao, Y. et al. (2004). Proc. Natl. Acad. Sci.USA 101, 7618-7623.)

The Rac subfamily has also been linked to cellular transformation and hence, the aberrant activity of Rho GTPases is associated with cancer. They play an essential role in transformation caused by Ras and other oncogenes. The Rac1b splice variant of Rac1 has been shown to be constitutively active and transforming; its overexpression has been observed in both breast and colon cancers (Qiu, R. G., et al. (1995) Nature 374, 457-459; Khosravi-Far, R., et al (1995) Mol. Cell. Biol. 15, 6443-6453; Renshaw, M. W. et al (1996) Curr. Biol. 6, 76-83; Ferraro, D., et al. (2006) Oncogene 25, 3689-3698). Rac3 mutants, for example, have been noted in brain tumors and both Rac1 and Rac3 have been linked to glioblastoma invasion (Hwang, S. L. et al (2005) J. Clin. Neurosci. 12, 571-574).

In malignant cells, aberrant Rho GTPase activity results from changes in the expression of Rho GTPases or the perturbed function of either GEFs or GAPs which regulate the function of Rho. (Karnoub, A. E. et al (2004). Breast Cancer Res. Treat. 84, 61-71.) Due to the evidence of Rho involvement in cell transformation, Rho GTPases are probable targets for anti-cancer therapies. Compounds that inhibit GEF interaction with their respective Rho family members would be useful inhibitors of Rho activity and exhibit great specificity. To date, small molecule NSC23766 (i.e., N6-[2-[[4-(diethylamino)-1-methylbutyl]amino]-6-methyl-4-pyrimidinyl]-2-methyl-4,6-quinolinediamine trihydrochloride) has been identified as binding to Rac1 and preventing its activation by Rac-specific RhoGEFs. Some GEF activity, however, was not blocked.

Chronic myelogenous leukemia (CML) is a malignant disease characterized by expression of p210-BCR-ABL, the product of the Philadelphia chromosome. Also known as chronic granulocytic leukemia (CGL), it is a cancer of the white blood cells and is characterized by the increased and upregulated growth of mainly myeloid cells in the bone marrow and the accumulation of these cells in the blood. The deficiency of the Rho GTPases Rac1 and Rac2 in a murine model has shown a significant reduction of p210-BCR-ABL-mediated proliferation. Rac has also been shown to play a role in other types of leukemias such as MLL-mediated acute leukemia. (Mizukawa B. et al., Blood 2011; 118:5235-45). The above evidence has strongly suggested Rac as a potential target for leukemia therapy. (E K Thomas et al, Leukemia 22, 898-904, May 2008).

SUMMARY

This disclosure is based on the discovery of certain anticancer compounds identified through analysis of docking onto the Rac-GTPase protein. In particular, one or more of these compounds identified by this assay unexpectedly exhibited superior activity in inhibiting proliferation of cancer cells with low toxicity to normal cells.

In one aspect, this disclosure features pharmaceutical compositions that include a pharmaceutically acceptable carrier and a compound of formula (I) or a salt thereof (e.g., as an active agent):

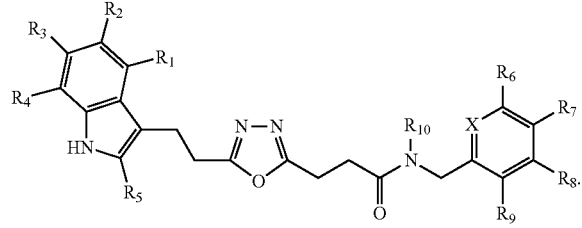

(I)

In formula (I), X is N or CH; each of $R_1$, $R_2$, $R_3$, $R_4$, and $R_5$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_a$, $C(O)NR_aR_b$, $S(O)_2NR_aR_b$, or $NR_aR_b$; each of $R_6$, $R_7$, $R_5$, and $R_9$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_a$, C(O)NR$_a$R$_b$, S(O)$_2$NR$_a$R$_b$, or NR$_a$R$_b$; or R$_6$ and R$_7$, R$_7$ and R$_5$, or R$_5$ and R$_9$, together with the carbon atoms to which they are attached, are aryl, heteroaryl, C$_3$-C$_{20}$ cycloalkyl, or C$_1$-C$_{20}$ heterocycloalkyl; R$_{10}$ is C$_1$-C$_{10}$ alkyl; each R$_a$, independently, is H, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, or heteroaryl; and each R$_b$, independently, is H, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, or heteroaryl.

Referring to formula (II), a subset of the compounds described above are those in which X is N. In such compounds, each of R$_1$, R$_2$, R$_3$, R$_4$, R$_5$, R$_6$, R$_7$, R$_8$, and R$_9$, independently, can be H or C$_1$-C$_{10}$ alkyl (e.g., CH$_2$CH$_3$). For example, in these compounds, R$_7$ can be CH$_2$CH$_3$ and R$_{10}$ can be CH$_3$. An example of such compounds

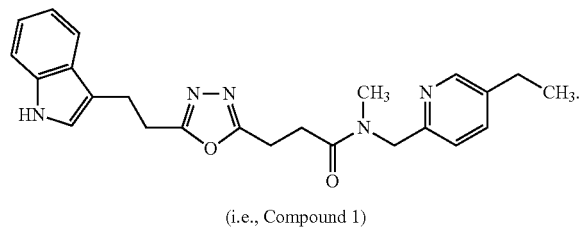 [SMILES: CCc1ccc(CN(C)C(=O)CCc2nnc(CCc3c[nH]c4ccccc34)o2)nc1]

(i.e., Compound 1)

Referring to formula (II), another subset of the compounds described above are those in which X is CH. In such compounds, each of R$_1$, R$_2$, R$_3$, R$_4$, R$_5$, R$_6$, R$_7$, R$_8$, and R$_9$, independently, can be H or C$_1$-C$_{10}$ alkyl (e.g., CH$_2$CH$_3$). For example, in these compounds, R$_7$ can be CH$_2$CH$_3$ and R$_{10}$ can be CH$_3$. An example of such compounds is

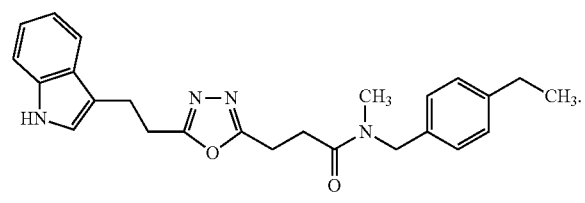

(i.e., Compound 2)

The term "alkyl" refers to a saturated, linear or branched hydrocarbon moiety, such as —CH$_3$ or —CH(CH$_3$)$_2$. The term "alkenyl" refers to a linear or branched hydrocarbon moiety that contains at least one double bond, such as —CH═CH—CH$_3$. The term "alkynyl" refers to a linear or branched hydrocarbon moiety that contains at least one triple bond, such as —C≡C—CH$_3$. The term "cycloalkyl" refers to a saturated, cyclic hydrocarbon moiety, such as cyclohexyl. The term "cycloalkenyl" refers to a non-aromatic, cyclic hydrocarbon moiety that contains at least one double bond, such as cyclohexenyl. The term "heterocycloalkyl" refers to a saturated, cyclic moiety having at least one ring heteroatom (e.g., N, O, or S), such as 4-tetrahydropyranyl. The term "heterocycloalkenyl" refers to a non-aromatic, cyclic moiety having at least one ring heteroatom (e.g., N, O, or S) and at least one ring double bond, such as pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

In some embodiments, the compositions described herein can further include an anti-cancer drug. For example, the anti-cancer drug can be Dexamethasone, Vincristine, or a PAK inhibitor.

In another aspect, this disclosure features a method for treating a Rac-GTPase mediated disorder. The method includes administering to a subject in need thereof an effective amount of one or more of the compounds described above. Examples of Rac-GTPase mediated disorders include cardiovascular diseases, immunodeficiency diseases, inflammatory disorders and cancer. Examples of Rac include Rac1, Rac2, and Rac3. Examples of Rac-GTPase include Rac1-GTPase, Rac2-GTPase, and Rac3-GTPase.

The term "treating" or "treatment" refers to administering one or more of the compounds described above to a subject who has an a disorder treatable with such compounds, and/or a symptom of such a disorder, and/or a predisposition toward such a disorder, with the purpose to confer a therapeutic effect, e.g., to cure, relieve, alter, affect, ameliorate, or prevent the above-described disorder, the symptom of it, or the predisposition toward it.

The compounds described herein include the compounds themselves, as well as their salts, prodrugs, and solvates, if applicable. Examples of prodrugs include esters and other pharmaceutically acceptable derivatives, which, upon administration to a subject, are capable of providing active compounds. A solvate refers to a complex formed between an active compound and a pharmaceutically acceptable solvent. Examples of pharmaceutically acceptable solvents include water, ethanol, isopropanol, ethyl acetate, acetic acid, and ethanolamine.

Also within the scope of this invention is a composition containing one or more of the compounds described above for use in treating an above-described disorder, and the use of such a composition for the manufacture of a medicament for the just-mentioned treatment.

The details of one or more embodiments are set forth in the description below. Other features, objects, and advantages will be apparent from the description, drawings, and claims.

DESCRIPTION OF DRAWINGS

FIG. 11b shows a Western Blot analysis of Compound 1 on RAS activation and a quantitation of pull down experiments obtained from DMSO, NSC23776, and Compound 1.

FIG. 14a shows the isobologram of a drug combination containing Compound 2 and Dexamethasone.

FIG. 14b shows the isobologram of a drug combination containing Compound 2 and Vincristine.

FIG. 14c shows the isobologram of a drug combination containing Compound 2 and PF-3758309.

DETAILED DESCRIPTION

Figure 1:
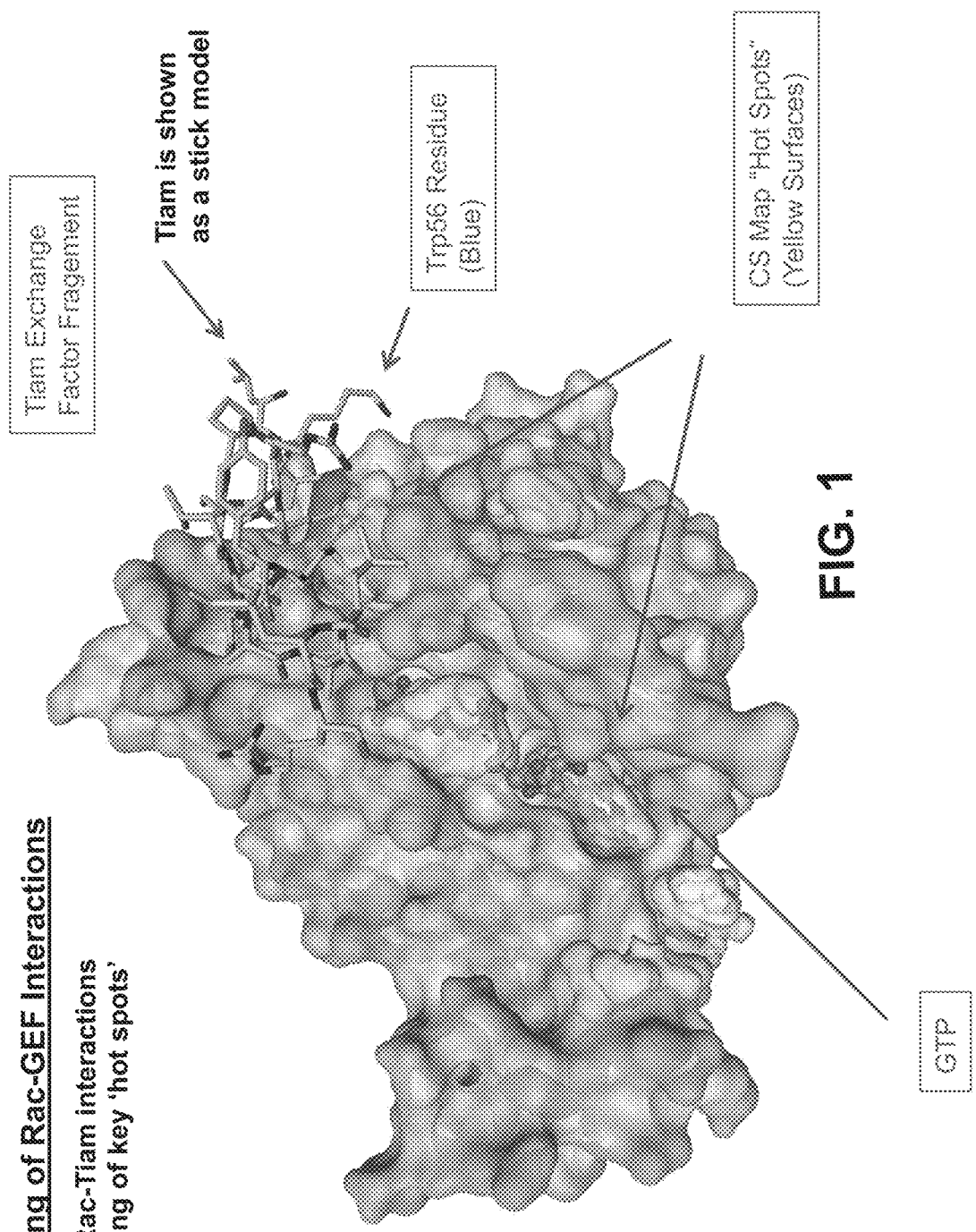
FIG. 1 depicts the in silico docking of interactions between Rac and its respective GEF, Tiam.

This disclosure relates to certain compounds identified as having anti-cancer activity using a quantitative, high throughput assay based on the interactions between the Rho family member Rac and its specific activator GEF, Tiam and the in silico docking of the compounds, individually, on the Rac 2 crystal structure. The compounds unexpectedly exhibit inhibition of leukemia cell proliferation in vitro and, in the case of certain compounds, minimal toxicity to normal bone marrow cells.

All of the compounds described herein can be prepared by methods well known in the art and/or obtained from a commercial source. For example, these compounds can be identified from Evotec AG's EVOsource databases and can be purchased from a commercial source such as Sigma-Aldrich (St. Louis, Mich.). A synthesized compound can be purified by a suitable method such as column chromatography, high-pressure liquid chromatography, or recrystallization.

The compounds described herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

The compounds can be identified by a screening method, such as an assay that identifies compounds that inhibit the proliferation of cancer cells. Alternatively or in addition, compounds can be identified using an assay that identifies compounds that inhibit the activation of the target protein (e.g., Rac-GTPase) and/or by the in silico analysis of the compound docking on the structure of the target protein.

For example, the screening method can include exposing a leukemia cell line (e.g., REM, SEM, MV411, RS411, Jurkat, Raji, Nomo-1, Maim6, or ML2) to various doses of the compound for various time periods. A candidate compound that inhibits cell survival can be identified based on the ability of the cell to proliferate in the presence of the compound. Such a screening method can be carried out in a container that includes the cells from a specific cell line, liquid media, and a candidate compound. The container can be, for example, a petri dish, a tissue culture flask, 24-well plate, a 48-well plate, a 96-well plate, a 384-well plate, a 1536-well plate, a 3456-well plate, or any other suitable container. In a high throughput screening method, each well of the container may contain a different candidate compound. As would be appreciated in the art, the screening method may be automated to obtain high throughput. For example, an MTS assay can be performed in liquid medium in standard microtiter plates. In addition, because manual screening of the plates can be slow, labor intensive and subjective, an automated staining method can be used in a high throughput screening method to distinguish live from dead cells.

The present disclosure also provides pharmaceutical compositions that include at least one (e.g., at least 2, 3, 4, 5, or at least 6) compound(s) depicted in formula (I), (e.g., compounds 1-2), or a pharmaceutically acceptable salt thereof, and a pharmaceutically acceptable carrier.

Compounds described herein can induce inhibition of proliferation. Induction of the inhibition of proliferation can mean inducing or enhancing the suppression of proliferation signals in a cell. For example, induction of the inhibition of proliferation can mean inducing or enhancing cell death in a cell. As another example, induction of the inhibition of proliferation can mean inducing or enhancing apoptosis in a cell. As another example, induction of the inhibition of proliferation can mean inducing or enhancing the state of quiescence in a cell. As yet another example, induction of the inhibition of proliferation can mean inducing or enhancing autophagy. Accordingly, compounds described herein can be used in methods of inducing the suppression of proliferation in a cell. The methods can include contacting a cell with a compound, salt, or composition described herein, in an amount effective to induce suppression of proliferation in the cell. The contacting can be done in vivo or in vitro.

In some embodiments, this disclosure features a method for treating a Rac-GTPase mediated disorder. The method includes administering to a subject (e.g., a patient) in need thereof an effective amount of a pharmaceutical composition containing one or more of the compounds described above. Examples of Rac-GTPase mediated disorders include cardiovascular disease, immunodeficiency diseases, inflammatory disorders and cancer.

The term "patient" is used throughout the disclosure to describe an animal, human or non-human, to whom treatment according to the methods described herein is provided. The term includes, but is not limited to, birds, reptiles, amphibians, and mammals, e.g., humans, other primates, pigs, rodents such as mice and rats, rabbits, guinea pigs, hamsters, cows, horses, cats, dogs, sheep and goats. Preferred subjects are humans, farm animals, and domestic pets such as cats and dogs.

Examples of cellular proliferative and/or differentiative disorders include cancer, such as carcinoma, sarcoma, metastatic disorders and hematopoietic neoplastic disorders, e.g., leukemias.

A metastatic tumor can arise from a multitude of primary tumor types, including but not limited to those of prostate, colon, lung, breast, bone, and liver origin. Metastases develop, e.g., when tumor cells shed from a primary tumor adhere to vascular endothelium, penetrate into surrounding tissues, and grow to form independent tumors at sites separate from a primary tumor.

The term "cancer" refers to cells having the capacity for autonomous growth. Examples of such cells include cells having an abnormal state or condition characterized by rapidly proliferating cell growth. The term is meant to include cancerous growths, e.g., tumors (e.g., solid tumors); oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation. The term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof.

Cancers that may be treated using the methods and compositions of the present disclosure include, for example, cancers of the stomach, colon, rectum, mouth/pharynx, esophagus, larynx, liver, pancreas, lung, breast, cervix uteri, corpus uteri, ovary, prostate, testis, bladder, skin, bone, kidney, brain/central nervous system, head, neck and throat; Hodgkins disease, non-Hodgkins leukemia, sarcomas, choriocarcinoma, and lymphoma, among others.

Individuals considered at risk for developing cancer may benefit particularly from the invention, primarily because prophylactic treatment can begin before there is any evidence of the disorder. Individuals "at risk" include, e.g., individuals exposed to carcinogens (e.g., by consumption such as by inhalation and/or ingestion) at levels that have been shown statistically to promote cancer in susceptible individuals. Also included are individuals at risk due to exposure to ultraviolet radiation, or their environment, occupation, and/or heredity, as well as those who show signs of a precancerous condition such as polyps. Similarly, individuals in very early stages of cancer or development of metastases (i.e., only one or a few aberrant cells are present in the individual's body or at a particular site in an individual's tissue)) may benefit from such prophylactic treatment.

Other examples of cellular proliferative and/or differentiative disorders that can be treated by the compounds described herein include inflammatory diseases and bone resorption disorders. Examples of inflammatory disorders include neurodegenerative disease, multiple sclerosis, systemic lupus erythematosus, rheumatoid arthritis, atherosclerosis, encephalitis, meningitis, hepatitis, nephritis, sepsis, sarcoidosis, psoriasis, eczema, uticaria, Type I diabetes, asthma, conjunctivitis, otitis, allergic rhinitis, chronic obstructive pulmonary disease, sinusitis, dermatitis, inflammatory bowel disease, ulcerative colitis, Crohn's disease, Behcet's syndrome, gout, viral infections, bacterial infections, organ transplant conditions, skin transplant conditions, graft rejection (including allograft rejection and graft-versus-host disease), spondyloarthropathies, scleroderma, vasculitis, and psoriasis (including T-cell mediated psoriasis). Other inflammatory disorders have been described in, e.g., U.S. Application Publication No. 20020155166, the entire contents of which are herein incorporated by reference.

In some embodiments, this disclosure features a method of treating unwanted angiogenesis in a patient. The method includes administering to a patient diagnosed as suffering from or at risk for unwanted angiogenesis an effective amount of a pharmaceutical composition containing one or more of the compounds described herein. The method can optionally include a step of identifying (e.g., diagnosing) the patient as suffering from or at risk for unwanted angiogenesis.

In some embodiments, this disclosure features a method of treating a condition associated with unwanted angiogenesis. The method includes administering to a patient diagnosed as suffering from or at risk for a condition associated with unwanted angiogenesis an effective amount of a pharmaceutical composition containing one or more of the compounds described herein, wherein the condition associated with unwanted angiogenesis is not cancer. The method can optionally include a step of identifying (e.g., diagnosing) the patient as suffering from or at risk for a condition associated with unwanted angiogenesis. In an embodiment, the condition is rheumatoid arthritis, lupus, psoriasis, diabetic retinopathy, retinopathy of prematurity, macular degeneration, corneal graft rejection, neovascular glaucoma, retrolental fibroplasia, rubeosis, Osler-Weber Syndrome, myocardial angiogenesis, plaque neovascularization, telangiectasia, or angiofibroma, or any combination thereof Methods of Treatment Skilled practitioners will appreciate that a patient can be diagnosed by a physician (or veterinarian, as appropriate for the patient being diagnosed) as suffering from or at risk for a condition described herein (e.g., cancer) by any method known in the art, such as by assessing a patient's medical history, performing diagnostic tests, and/or by employing imaging techniques.

Skilled practitioners will also appreciate that compositions described herein need not be administered to a patient by the same individual who diagnosed the patient (or prescribed the composition for the patient). The compositions can be administered (and/or administration can be supervised), e.g., by the diagnosing and/or prescribing individual, and/or any other individual, including the patient her/himself (e.g., where the patient is capable of self-administration).

Amounts of the composition effective to treat a disorder described herein (e.g., cancer) can be administered to (or prescribed for) a patient, e.g., by a physician or veterinarian, on the day the patient is diagnosed as suffering any of these disorders or conditions, or as having any risk factor associated with an increased likelihood that the patient will develop such disorder(s) or condition(s) (e.g., the patient has recently been, is being, or will be exposed to a carcinogen(s)). The composition can be administered to the patient intermittently or continuously. For example, the composition can be administered for at least about 1, 2, 4, 6, 8, 10, 12, 14, 18, or 20 days, or greater than 20 days (e.g., 1 2 3, 5, or 6 months) or until the patient no longer exhibits symptoms of the condition or disorder, or until the patient is diagnosed as no longer being at risk for the condition or disorder. In a given day, a composition can be administered continuously for the entire day, or intermittently or for up to 23 hours per day, e.g., up to 20, 15, 12, 10, 6, 3, or 2 hours per day, or up to 1 hour per day.

If the patient needs to be treated with chemotherapy, radiation therapy, immunotherapy, gene therapy, and/or surgery (e.g., because prescribed by a physician or veterinarian), the patient can be treated with a composition described herein before, during, and/or after administration of the chemotherapy, radiation therapy, and/or surgery. For example, with regard to chemotherapy, immunotherapy, gene therapy, and radiation therapy, a composition can be administered to the patient, intermittently or continuously, starting 0 to 20 days before the chemotherapy, immunotherapy, gene therapy, or radiation therapy is administered (and where multiple doses are given, before each individual dose), e.g., starting at least about 30 minutes (e.g., about 1, 2, 3, 5, 7, or 10 hours, or about 1, 2, 4, 6, 8, 10, 12, 14, 18, or 20 days, or greater than 20 days) before the administration. Alternatively or in addition, the composition can be administered to the patient concurrent with administration of chemotherapy, immunotherapy, gene therapy, or radiation therapy. Alternatively or in addition, the composition can be administered to the patient after administration of chemotherapy, immunotherapy, gene therapy, or radiation therapy, e.g., starting immediately after administration, and continuing intermittently or continuously for about 1, 2, 3, 5, 7, or 10 hours, or about 1, 2, 5, 8, 10, 20, 30, 50, or 60 days, one year, indefinitely, or until a physician determines that administration of the composition is no longer necessary. With regard to surgical procedures, the composition can be administered systemically or locally to a patient prior to, during, and/or after a surgical procedure is performed. The composition can be administered to the patient intermittently or continuously, for 1 hour, 2, hours, 3 hours, 4 hours, 6, hours, 12 hours, or about 1, 2, 4, 6, 8, 10, 12, 14, 18, or 20 days, or greater than 20 days, before the procedure. It can be administered in the time period immediately prior to the surgery and optionally continue through the procedure, or the administration can cease at least 15 minutes before the surgery begins (e.g., at least 30 minutes, 1 hour, 2 hours 3 hours, 6 hours, or 24 hours before the surgery begins). Alternatively or in addition, the composition can be administered to the patient during the procedure, e.g., by topical administration. Alternatively or in addition, the composition can be administered to the patient after the procedure, e.g., starting immediately after completion of the procedure, and continuing for about 1, 2, 3, 5, 7, or 10 hours, or about 1, 2, 5, 8, 10, 20, 30, 50, or 60 days, 1 year, indefinitely, or until the patient no longer suffers from, or is at risk for, cancer after the completion of the procedure.

Treatments for B-cell chronic lymphocytic leukemia (B-CLL) can include administration of combination chemotherapeutic regimens. In many instances, combinations of fludarabine with alkylating agents or with monoclonal antibodies can be used for the treatment of B-CLL. For example, fludarabine can be administered in a combination therapy with alkylating agents such as cyclophosphamide or bendamustine. Fludarabine can also be administered in combination with monoclonal antibodies such as alemtuzumab, rituximab, or ofatumumab. Fludarabine can also be administered for the treatment of B-CLL in combination with all of the following: an alkylating agent, an anthracycline antibiotic, a *vinca* alkyloid, and a corticosteroid. For example, fludarabine can be administered together with cyclophosphamide, doxorubicin, vincristine and prednisolone.

Treatments for acute lymphoblastic leukemia (ALL) can include administration of the following: prednisone, vincristine, anthracyclines, L-asparaginase, cyclophosphamide.

Treatments for chronic myelogenous leukemia (CML) can include the administration of imatinib. Treatments for prolymphocytic leukemia can include purine analogues, chlorambucil, and various chemotherapy including: cyclophosphamide, doxorubicin, vincristine, prednisone cyclophosphamide, doxorubicin, vincristine and prednisolone, etoposide, bleomycin VAPEC-B, and Alemtuzumab.

Treatments for the diseases encompassing leukemia can include the following therapeutic agents and combinations of these therapeutic regimens: In many instances, combinations of fludarabine, alkylating agents such as cyclophosphamide or bendamustine, monoclonal antibodies such as alemtuzumab, rituximab, or ofatumumab, an anthracycline antibiotic such as doxirubicin, a *vinca* alkyloid, anthracyclines, L-asparaginase, cyclophosphamide, imatinib, purine analogues, chlorambucil, cyclophosphamide, doxorubicin, vincristine, prednisone cyclophosphamide, doxorubicin, vincristine and prednisolone, etoposide, bleomycin VAPEC-B, and Alemtuzumab and/or a corticosteroid.

Combination Therapy

In some embodiments, a compound described in the present disclosure, or a pharmaceutically acceptable salt thereof, can be used in combination with another therapeutic agent to treat diseases such as cancer. For example, the additional agent can be a therapeutic agent that is art-recognized as being useful to treat the disease or condition being treated by the compound described above. In some embodiments, the additional agent can be an anti-cancer drug, such as Dexamethasone, Vincristine, or a PAK inhibitor (e.g., PF-3758309 described in Murray et al., PNAS, Vol. 107, No. 20, 9446-9451 (2010)). The additional agent also can be an agent that imparts a beneficial attribute to the therapeutic composition (e.g., an agent that affects the viscosity of the composition).

The combination therapy contemplated by this disclosure includes, for example, administration of one or more compound described herein, or a pharmaceutically acceptable salt thereof, and additional agent(s) in a single pharmaceutical formulation or in separate pharmaceutical formulations. Alternatively or in addition, combination therapy can include administering at least two compounds described herein, or pharmaceutically acceptable salts thereof, in the same or separate pharmaceutical formulations. In other words, co-administration shall mean the administration of at least two agents to a subject so as to provide the beneficial effects of the combination of both agents. For example, the agents may be administered simultaneously or sequentially over a period of time.

In some embodiments, the methods described herein can be used in combination with the therapies and combination therapies recited above.

Pharmaceutical Formulations and Dosage Forms

When employed as pharmaceuticals, the compounds described in the present application can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also within the scope of this disclosure are pharmaceutical compositions containing at least one compound described above and a pharmaceutical acceptable carrier. Further, this disclosure covers a method of administering an effective amount of the compounds described herein, e.g., in a pharmaceutical composition, to a patient having cancer, e.g., as described herein. "An effective amount" or "an amount effective" refers to the amount of an active compound that is required to confer a therapeutic effect on the treated patient. Effective doses will vary, as recognized by those skilled in the art, depending on the types of diseases treated, route of administration, excipient usage, and the possibility of co-usage with other therapeutic treatment.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the treatment method described herein, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typical doses can range from about 0.01 μg/kg to about 50 mg/kg (e.g., from about 0.1 μg/kg to about 25 mg/kg, from about 1 μg/kg to about 10 mg/kg, from about 10 μg/kg to about 5 mg/kg, or from about 0.1 mg/kg to about 1 mg/kg) of body weight per day. In some embodiments, suitable daily doses can range from about 10 μg/kg to about 100 μg/kg of body weight.

To practice the method described in the present disclosure, a composition having one or more compounds described above can be administered parenterally, orally, nasally, rectally, topically, and/or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in buffered saline or 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as TWEENs or SPANs or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active compounds described above can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound described above. Examples of other carriers include colloidal silicon oxide, magnesium stearate, cellulose, sodium lauryl sulfate, and D&C Yellow #10.

The therapeutic compounds can also be prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Methods of formulating suitable pharmaceutical compositions are known in the art. See, e.g., the books in the series *Drugs and the Pharmaceutical Sciences: a Series of Textbooks and Monographs* (Dekker, N.Y.).

The compounds described above can be preliminarily screened for their efficacy in treating above-described diseases by the screening method described herein and then confirmed by additional animal experiments and/or clinic trials. Other screening methods will also be apparent to those of ordinary skill in the art.

Synthesis

Compounds described in this disclosure, including salts thereof, can be prepared using known organic synthesis techniques and can be synthesized according to any of numerous possible synthetic routes, for example, by methods analogous to those of Gerard et al. *ACS Comb. Sci.* 2011, 13, 365.

The reactions for preparing compounds of the present application can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds described in the present application can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present application. Cis and trans geometric isomers of the compounds of the present application are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the present application also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described in the present application can also include all isotopes of atoms occurring in the intermediates or final compounds. Isotopes include those atoms having the same atomic number but different mass numbers. For example, isotopes of hydrogen include tritium and deuterium.

All compounds and pharmaceutically acceptable salts thereof, can be found together with other substances such as water and solvents (e.g. hydrates and solvates) or can be isolated.

In some embodiments, the compounds described in the present application, or salts thereof, are substantially isolated. By "substantially isolated" is meant that the compound is at least partially or substantially separated from the environment in which it was formed or detected. Partial separation can include, for example, a composition enriched in the compounds described in the present application. Substantial separation can include compositions containing at least about 50%, at least about 60%, at least about 70%, at least about 80%, at least about 90%, at least about 95%, at least about 97%, or at least about 99% by weight of the compounds described in the present application, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Kits

The present application also includes pharmaceutical kits useful, for example, in the treatment or prevention of a Rac-GTPase mediated disorder (e.g. cancer), which include one or more containers containing a pharmaceutical composition comprising a therapeutically effective amount of a compound of the present application. Such kits can further include, if desired, one or more of various conventional pharmaceutical kit components, such as, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The contents of all publications cited herein (e.g., patents, patent application publications, and articles) are hereby incorporated by reference in their entirety.

EXAMPLES

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

Example 1: In Silico Screen for Rae Inhibitors

Methods

Rac-GEF interactions In order to perform a virtual screen for Rac inhibitors, an in silico docking on a Rac2 crystal structure is required. An in silico docking of Rac-GEF interactions was done to decipher potential target sites on the Rac protein on which small molecule binding would result in an interruption in GEF interaction with the protein. FIG. 1 shows a model of the GEF TIAM with RAC (TIAM-Rac). Rac is shown in gray and TIAM is depicted as a stick model. The Trp56 residue of Tiam is highlighted in blue. Mapped are the 'hot spots' which are potential locations of interrupting Rac-GEF interactions. The mapped 'hot spots', defined as the target locations at which Tiam and Rac have significant interaction, are shown as yellow surfaces. A GTP molecule is also present.

in silico screen A screen of 14 million compounds from the Evotex AG library was performed. Specific filters for drug-like characteristics yielded 4.8 million compounds. These compounds were selected for docking. An in-house algorithm was applied to maximize chemical diversity among the chosen compounds. In silico docking of the compounds on the Rac2 crystal structure and the top 1.2 million compounds were selected for further evaluation. This represented the top 30% of the compounds selected. These compounds were analyzed in two groups. The first group of compounds was analyzed by the docking of the compounds on the Rac1 structure and selected based on a similar binding mode both in Rac-1 and Rac-2, a high docking score both in Rac1 and Rac2 and pharmacophore matching with the binding hypotheses for the known active compounds. Analysis of the second group involved re-scoring the docking poses using ASP and Chemscore scoring functions and selecting compounds with high scoring values for all the 3 scoring methods, i.e. Gold, ASP, Chemsc.

Results Upon selecting a diverse collection and following visual inspection, 75 compounds were chosen from Group 1. Upon selecting a diverse collection and following visual inspection, 77 compounds were chosen from Group 2. Of these 152 prioritized compounds, 100 of these were purchased from a commercial source for further screening.

Example 2: Selection of Lead Compound

Dose Dependent Inhibition of Proliferation The 100 compounds selected from the initial in silico screen were assayed for inhibition of proliferation in two leukemia cell lines, SEM and P12 by Cell Titer Glo. The cells for the proliferation assay were spun down and re-suspended. The cell suspension was then divided and the compound to be tested added in desired concentrations and subsequently plated. Following an incubation period, the Cell Titer Glo reagent (Promega CellTiter 96® Aqueous Non-Radioactive Cell Proliferation Assay) was added and allowed to incubate. The absorbance is subsequently measured at 490 nm using a plate reader. Each compound was analyzed for its effects on cell proliferation.

To determine which of these compounds should be further pursued, a biochemical pull down assay was performed to confirm specific inhibition of Rac activation indicated by disruption of the interaction between Rac and GTPase. The assay initially required treatment of cells followed by pull down and analysis with Western blot. The cells were first starved in serum free media for 2 hours. They were then re-suspended in serum-containing medium and inhibitors added at desired concentration. Following incubation for the desired length of time, the cells were pelleted and lysed with Magnesium Lysis Buffer (Millipore $Mg^{2+}$ lysis/wash buffer). The Rac protein and any bound proteins were then collected with Pak Beads (Millipore Rac/cdc42 Assay Reagent (PAK-1 PBD, agarose). Bound protein was subsequently removed with lysis buffer and subject to Western Blot analysis.

Figure 2A:
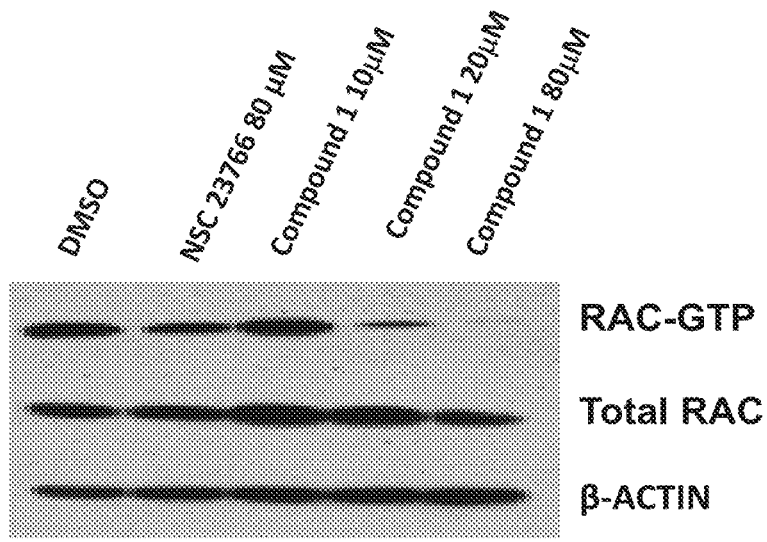
FIG. 2a shows a Western Blot analysis indicating that Compound 1 resulted in dose dependent reduction of Rac activation, but had no significant effect on total Rac levels.
Figure 2B:
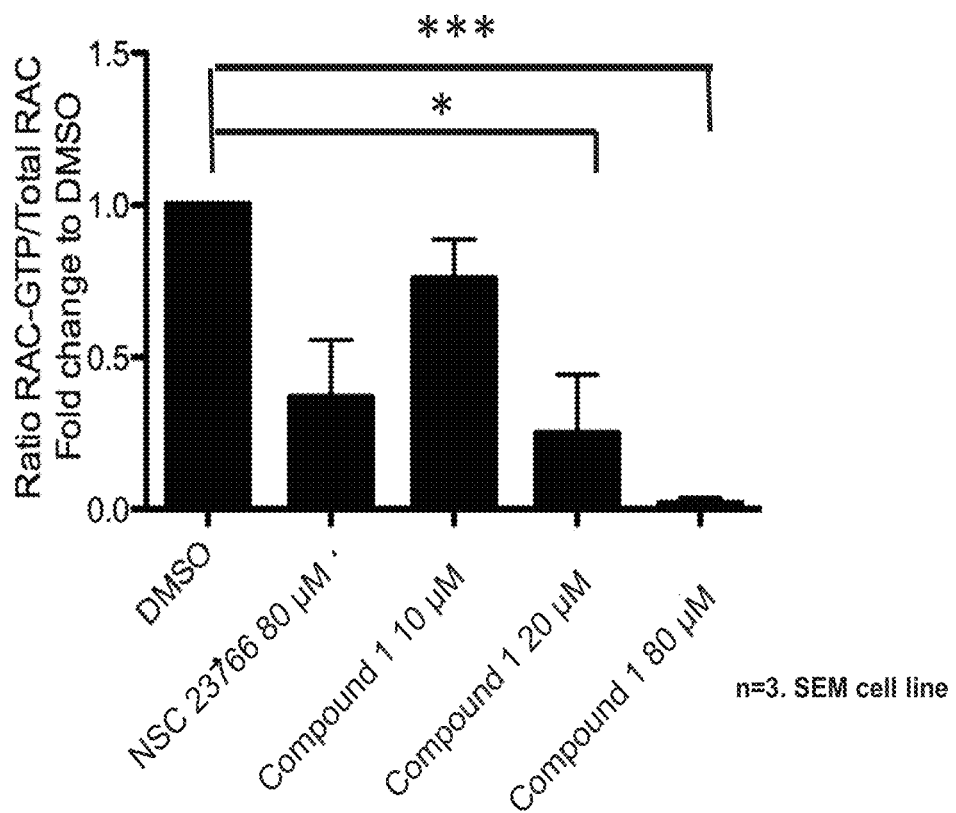
FIG. 2b shows a quantitation of pull down experiments obtained from DMSO, NSC23766, and Compound 1.

Compound 1 was identified as a lead compound from the above analyses. FIG. 2a shows a Western Blot analysis indicating that Compound 1 resulted in dose dependent reduction of Rac activation, but had no significant effect on total Rac levels. FIG. 2b shows a quantitation of three independent pull down experiments obtained from Compound 1. The Western Blot and pull down analyses are also shown for the compound DMSO, and the compound NSC23776, which is a known inhibitor of Rac1 binding and of Rac activation by Rac-specific RhoGEFs.

Example 3: Analysis of Compound 1 of its Efficacy in Inhibiting Leukemia Cell Lines The lead compound, i.e. Compound 1, was analyzed for its effect on cell proliferation at various doses on three different leukemia cell lines: SEM, P12, and Loucy. In order to quantitate the percentage inhibition of cell proliferation, Cell Titer Glo analysis was completed as described in Example 2 above.

Figure 3C:
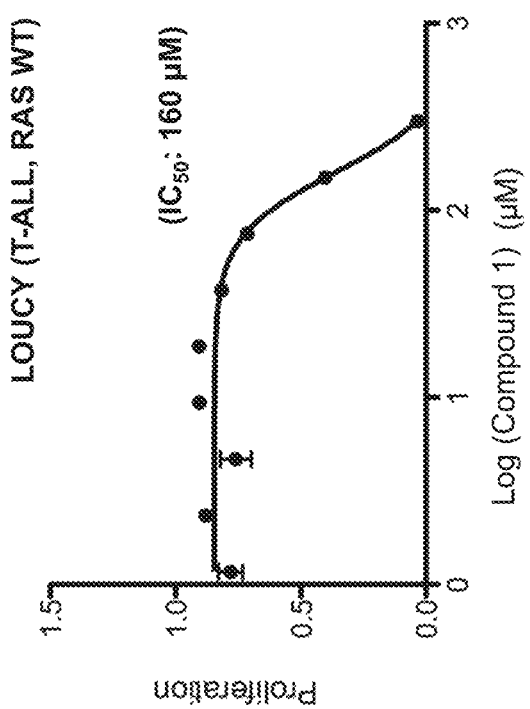
FIG. 3c shows a graph illustrating the dose dependent inhibition of proliferation of Compound 1 in Loucy cells as measured by MTS assay.
Figure 3A:
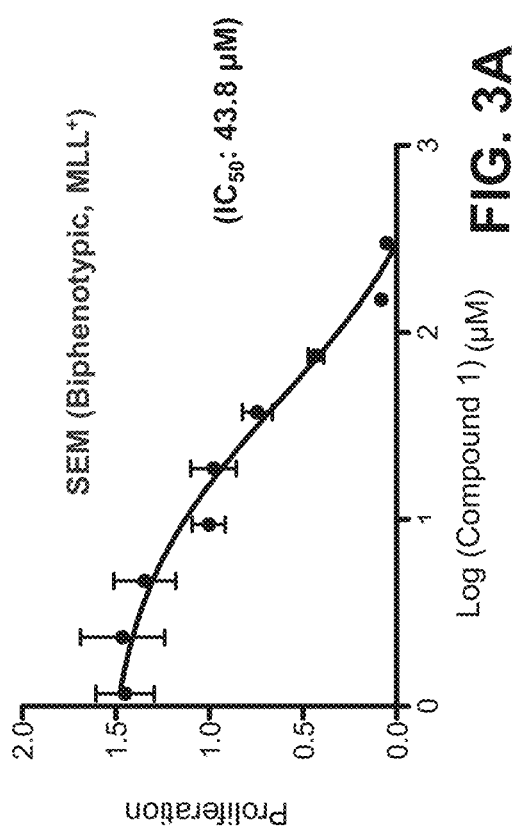
FIG. 3a shows a graph illustrating the dose dependent inhibition of proliferation of Compound 1 in SEM cells as measured by MTS assay.
Figure 3B:
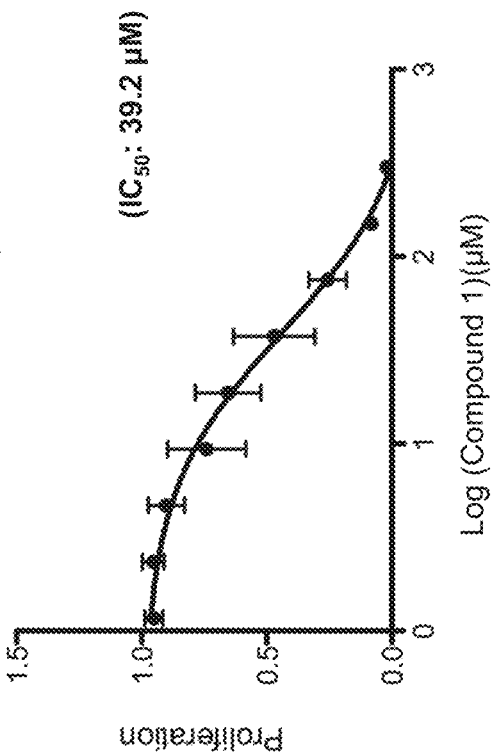
FIG. 3b shows a graph illustrating the dose dependent inhibition of proliferation of Compound 1 in P12-Ichikawa cells as measured by MTS assay.
Figure 4A:
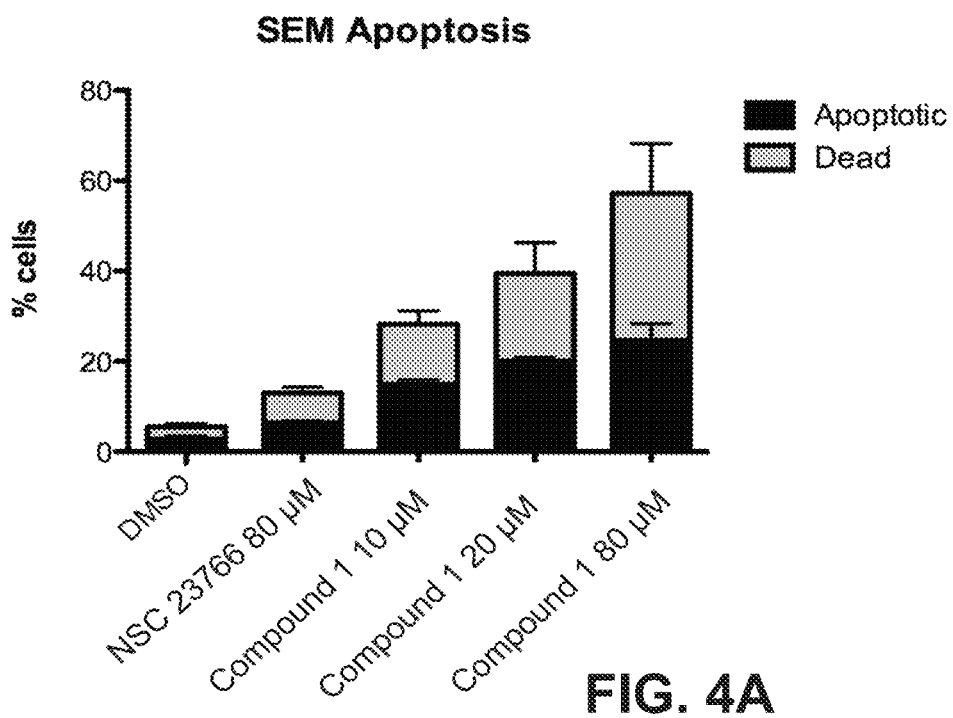
FIG. 4a shows the effect of DMSO, NSC23766, and Compound 1 on cells apoptosis and cell death in SEM cell line.
Figure 4B:
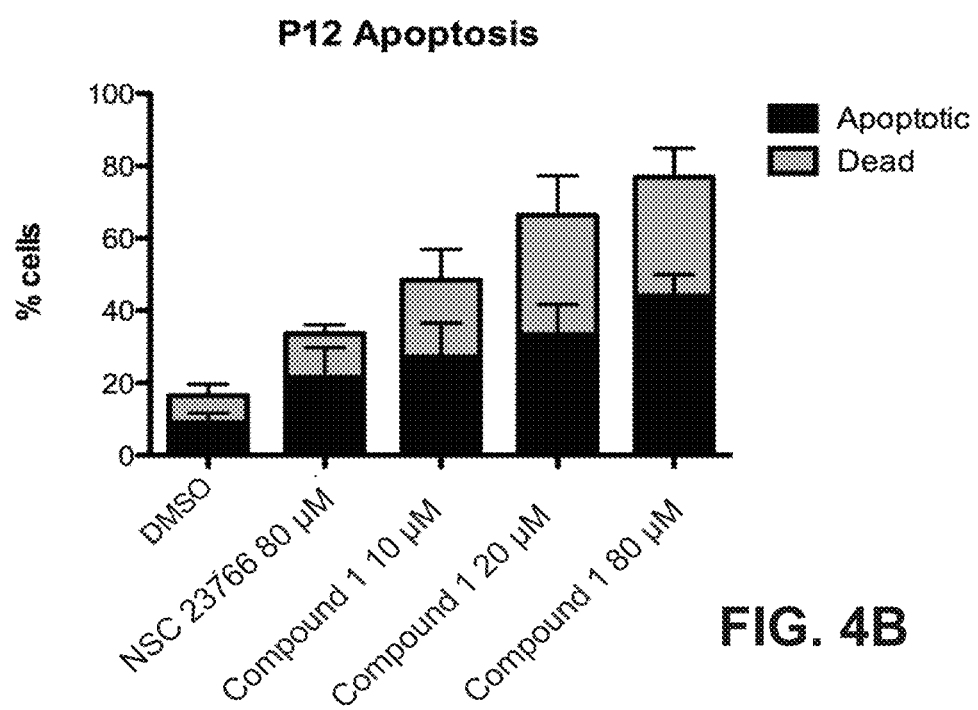
FIG. 4b shows the effect of DMSO, NSC23766, and Compound 1 on cells apoptosis and cell death in P12 cell line.

FIGS. 3a-3c show three graphs illustrating the dose dependent inhibition of proliferation of Compound 1 in SEM, P12, and Loucy cells as measured by MTS assay. As shown in these three figures, Compound 1 exhibited IC50 value of 43.8 μM, 39.2 μM, and 160 μM against SEM, P12, and Loucy cells, respectively. Compound 1 was further analyzed for its effect on cell apoptosis and cell death using a flow based assay using Annexin V staining. The results are shown in FIGS. 4a and 4b, which shows the effect of DMSO, NSC23766, and Compound 1 on apoptosis and cell death in SEM and P12 cell lines. As shown in these two figures, Compound 1 caused cells apoptosis and cell death in SEM and P12 cell lines in a dose-dependent manner.

Example 4: Evaluation of Compound 1 for its Toxicity

Figure 5:
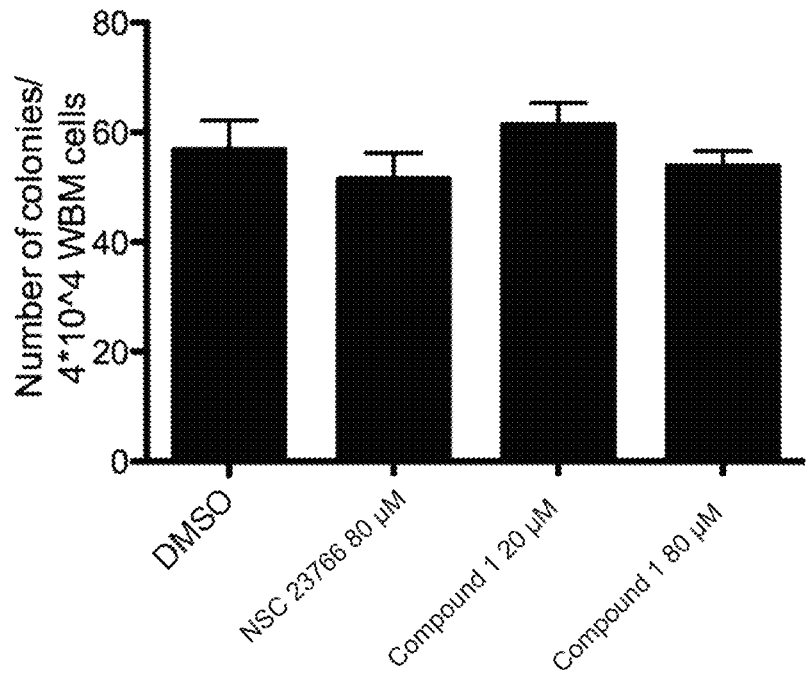
FIG. 5 shows the toxicity test results of DMSO, NSC23766, and Compound 1 in a colony forming unit assay.

Compound 1 was tested for toxicity in a colony forming unit assay (CFU assay), which was performed by plating normal bone marrow hematopoietic and progenitor cells in semi-solid media supplemented with different doses of Compound 1, NSC23766, and DMSO. The test results are shown in FIG. 5. As shown in FIG. 5, Compound 1 did not exhibit toxicity toward normal bone marrow cells.

Example 5: In Vivo Assay for Evaluating Pharmacokinetics and Anti-Leukemia Activities of Compound 1

Figure 6:
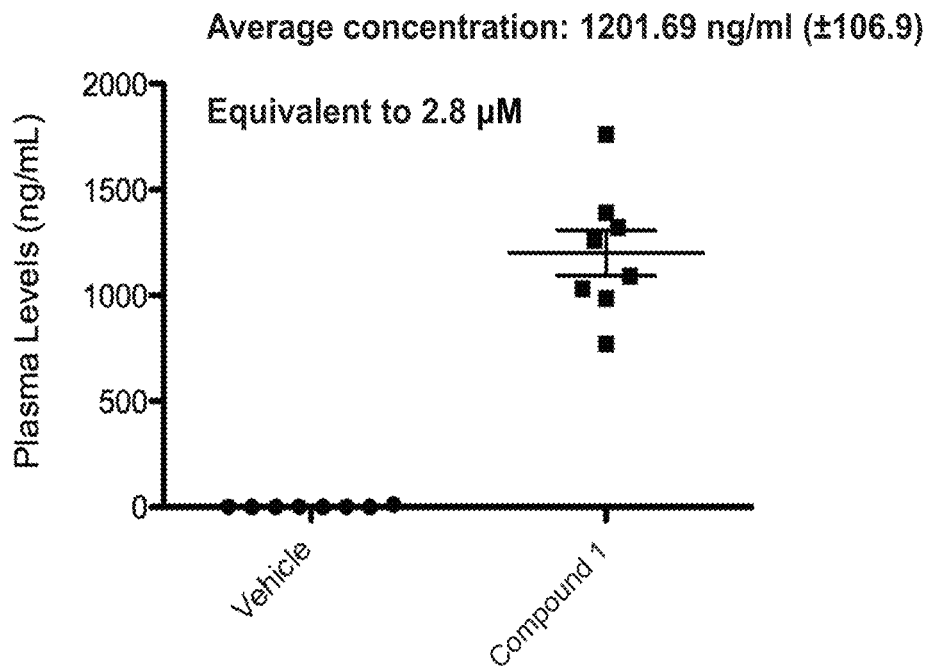
FIG. 6 shows the plasma levels of Compound 1 or a vehicle after the last administration in leukemia mice treated with Compound 1 at a dose 250 mg/Kg or the vehicle for 21 days twice a day.
Figure 7:
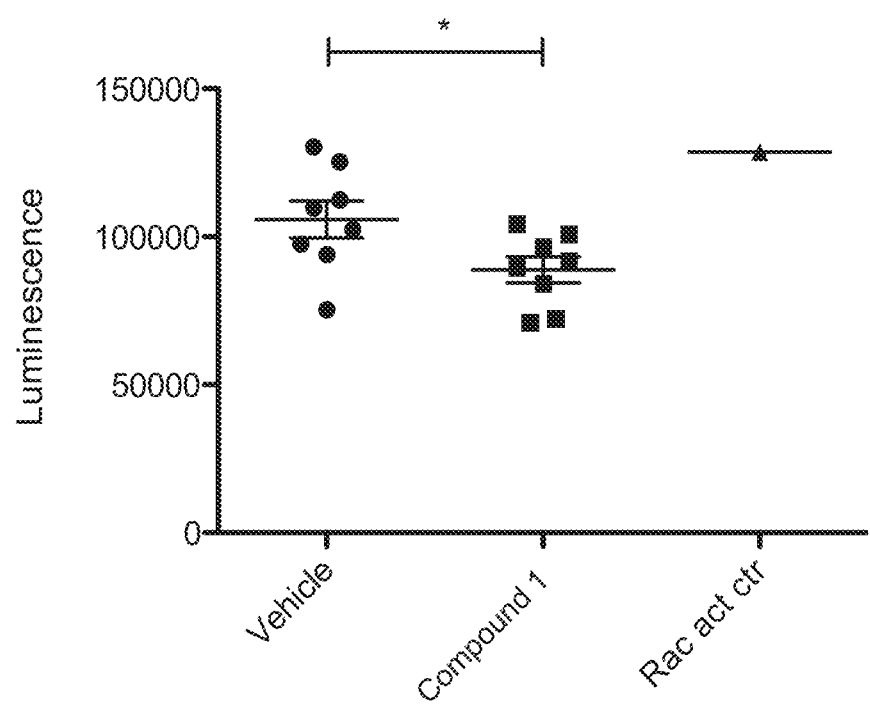
FIG. 7 shows the Rac activation status as determined by using an Elisa assay on spleen infiltrated by leukemic blasts in mice treated with Compound 1 or a vehicle.

Compound 1 was assayed for its pharmacokinetics and anti-leukemia activities in mice. Specifically, a SEM leukemic cell line was labeled with a vector encoding the mCherry tag and Luciferase. 500,000 labeled cells were injected into immunodeficient mice (NSG mice). After establishment of leukemia (as assessed by bioluminescent imaging), mice were treated with Compound 1 at a dose 250 mg/Kg or a vehicle for 21 days twice a day. During treatment, mice were imaged every other day and BLI recorded and analyzed. 2 hours after the last dose, animals were sacrificed and organs harvested for PK and PD analysis. FIG. 6 shows the plasma levels of Compound 1 after the last administration. FIG. 7 shows the Rac activation status as determined by using an Elisa assay on spleen infiltrated by leukemic blasts in mice treated with Compound 1 or a vehicle. As shown in the graph on the right in FIG. 7, Compound 1 reduced Rac activation compared to a vehicle.

Figure 8:
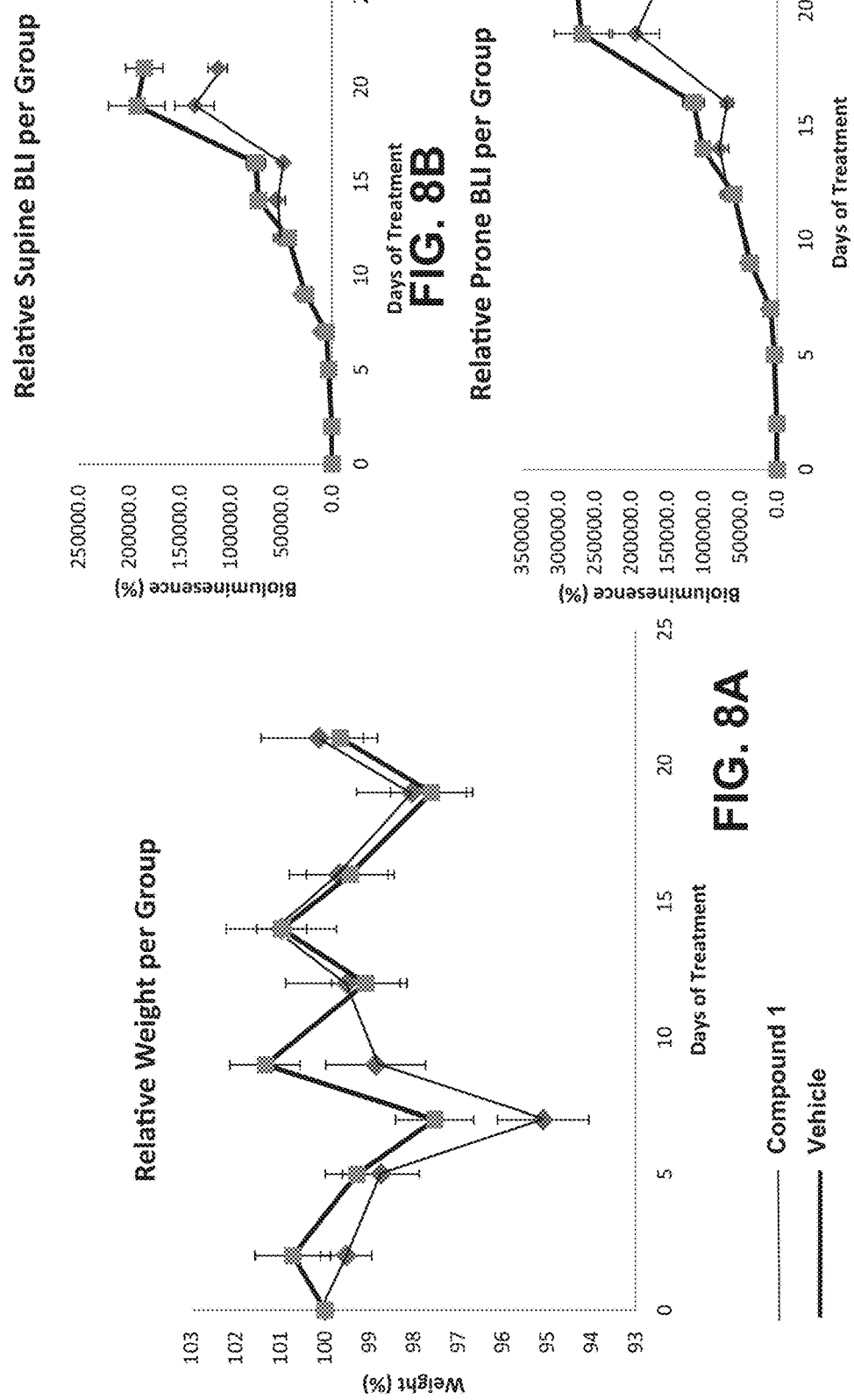
FIG. 8a shows the relative weight of the mice in the groups treated with Compound 1 and a vehicle.
FIG. 8b shows the bioluminescence data obtained from the mice treated with Compound 1 and a vehicle when the mice were imaged in a supine position.
FIG. 8c shows the bioluminescence data obtained from the mice treated with Compound 1 and a vehicle when the mice were imaged in a prone position.
Figure 9:
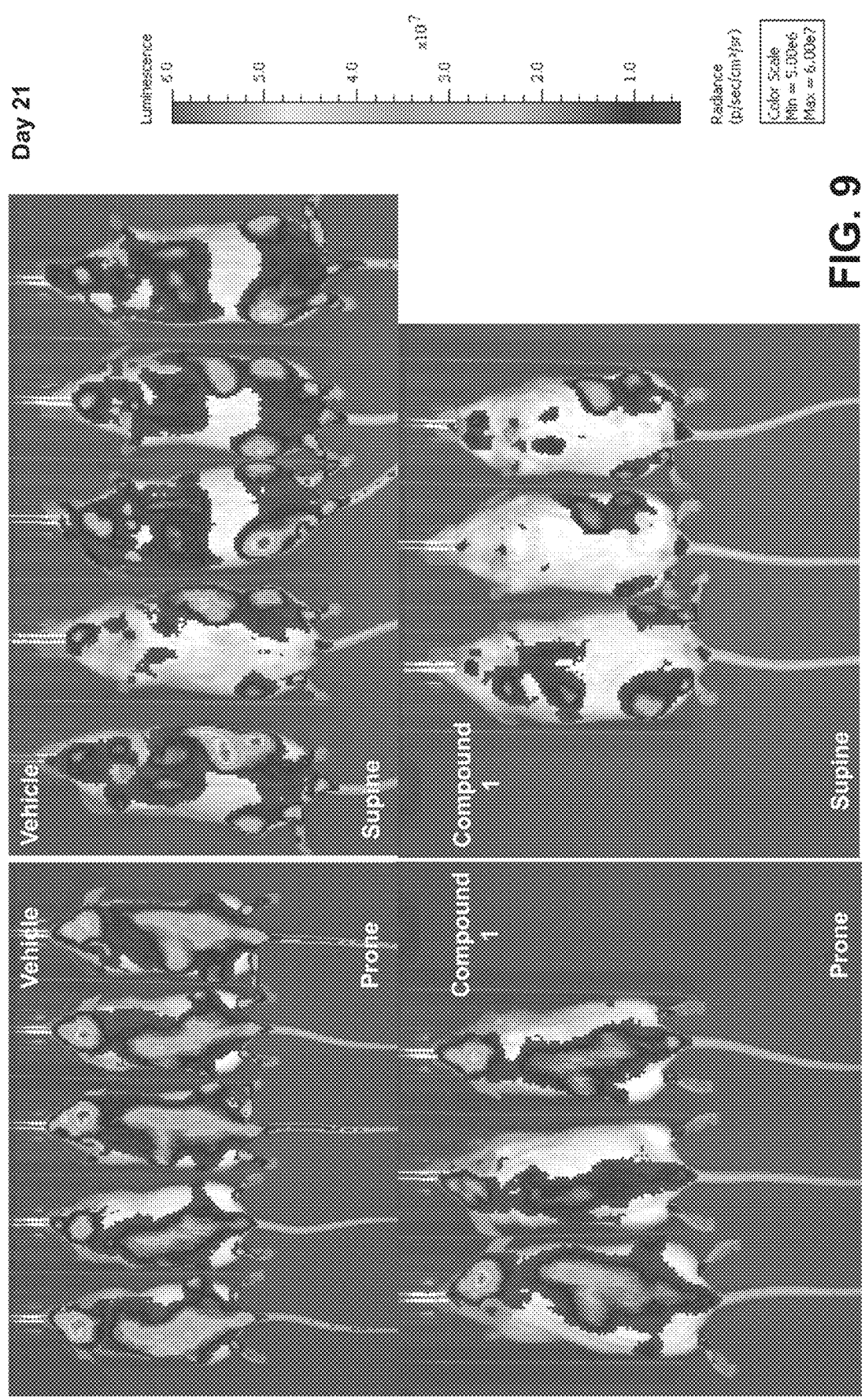
FIG. 9 shows representative actual images obtained after mice in the groups treated with Compound 1 and a vehicle for 21 days when the mice were imaged in a supine position and a prone position.

Further, FIG. 8a shows the relative weight of the mice in the groups treated with Compound 1 and a vehicle. As shown in FIG. 8a, the relative weights of the mice in these two groups (i.e., each of which is based on the average weight of the mice in each group and normalized to the average weight before treatment) are nearly identical, suggesting that Compound 1 exhibited no or low toxicity. FIGS. 8b and 8c show the bioluminescence data obtained from the mice treated with Compound 1 and a vehicle when the mice were imaged in a supine position and a prone position, respectively. As shown in these two figures, Compound 1 significantly reduced the bioluminescence in the mice when imaged in either position, suggesting that this compound effectively inhibited leukemia proliferation. FIG. 9 shows representative actual images obtained after mice in the groups treated with Compound 1 and a vehicle for 21 days when the mice were imaged in a supine position and a prone position.

Figure 10A:
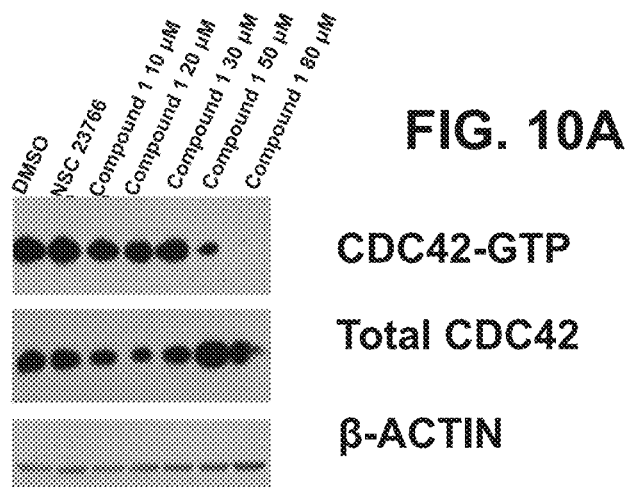
FIG. 10a shows a Western Blot analysis indicating that Compound 1 resulted in dose dependent reduction of CDC42 activation, but had no significant effect on total CDC42 levels.
Figure 10B:
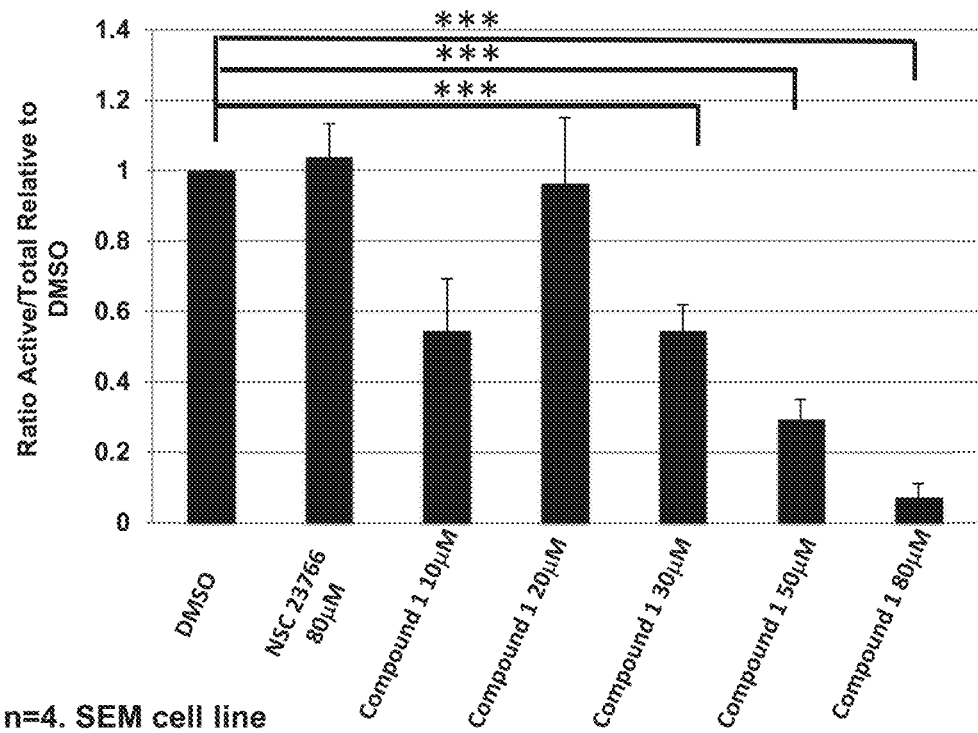
FIG. 10b shows a quantitation of pull down experiments obtained from DMSO, NSC23766, and Compound 1.

Example 6: Evaluation of Compound 1 for its Effect on CDC42, RHOA, and RAS Activation Compound 1 was tested to evaluate its effect on CDC42 activation. In this case, beads for the immunoprecipitation were coated with a CDC42 effector domain. FIG. 10a shows a Western Blot analysis indicating that Compound 1 resulted in dose dependent reduction of CDC42 activation, but had no significant effect on total CDC42 levels. FIG. 10b shows a quantitation of five independent pull down experiments obtained from Compound 1. The Western Blot and pull down analyses are also shown for DMSO and NSC23776.

Figure 11A:
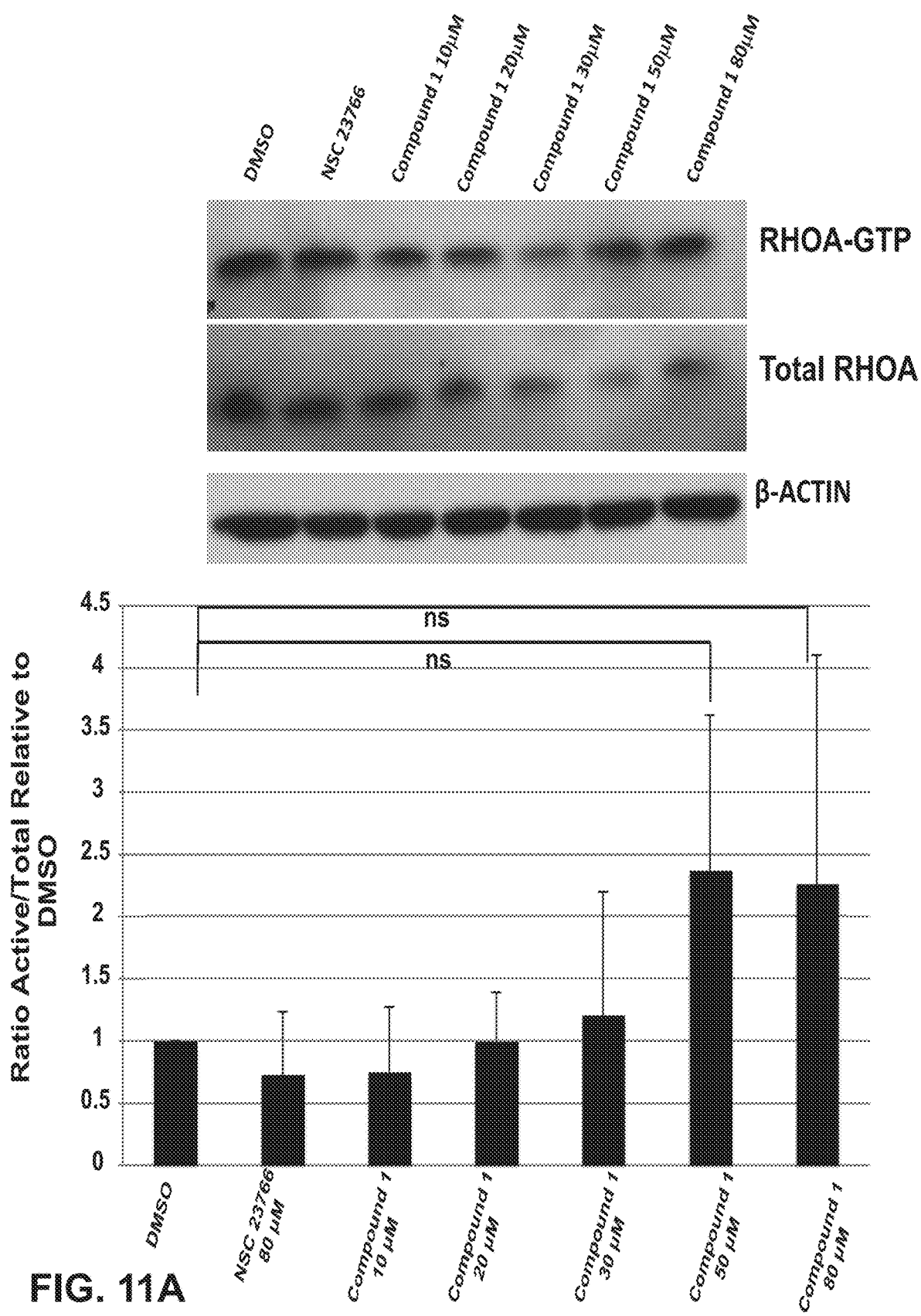
FIG. 11a shows a Western Blot analysis of Compound 1 on RHOA activation and a quantitation of pull down experiments obtained from DMSO, NSC23776, and Compound 1.

Compound 1 was further tested to evaluate its effect on RHOA and RAS activation. FIG. 11a shows a Western Blot analysis of Compound 1 on RHOA activation and a quantitation of pull down experiments obtained from DMSO, NSC23776, and Compound 1. FIG. 11b shows a Western Blot analysis of Compound 1 on RAS activation and a quantitation of pull down experiments obtained from DMSO, NSC23776, and Compound 1. As shown in FIGS. 11a and 11b, Compound 1 had no significant effect on RHOA or RAS activation.

Example 7: Evaluation of Binding Between Compound 1 and Rac1

Compound 1 was tested for its efficacy in binding with Rac1 in two independent binding assays, i.e., 2D NMR spectroscopy and Homologous time resolved fluorescence assay (HTRF).

In the 2D NMR assay, samples containing 50 µM Rac1 and 250 µM or 400 µM Compound 1 were used. The NMR spectra obtained from the above samples did not indicate any binding of this compound to Rac1. Further, no binding was observed in the HTRF assay.

In sum, the results above suggest that Compound 1 does not substantially bind to Rac1. In view of the results shown in this Example and in Example 6, without wishing to be bound by theory, it is believed that Compound 1 inhibits Rac1 activation by binding to a protein upstream of Rac1.

Example 8: Kinase Screening and GPCR Profiling for Compound 1

Compound 1 was tested for its efficacy in inhibiting activities of 40 kinases and binding with 12 GPCRs both as an antagonist and an agonist. The kinase inhibiting percentage of Compound 1 and NSC23766 are shown in Table 1 below. The GPCR binding percentage of Compound 1 and NSC23766 are shown in Table 2 below. As shown in Tables 1 and 2, Compound 1 exhibited no significant inhibition of the 40 kinases tested and no significant binding to the 12 GPCRs tested, suggesting that this compound has no off target effects on the analyzed proteins.

TABLE 1

Kinase Screening Results

| Kinase | NSC23766 (inhibition percentage) | Compound 1 (inhibition percentage) |
|---|---|---|
| PIK3C2A (PI3K-C2 alpha) | −3.3 | −1.3 |
| PIK3C2B (PI3K-C2 beta) | −1.8 | −10.9 |
| PIK3C3 (hVPS34) | −17.8 | −12.5 |
| PIK3CA/PIK3R1 (p110 alpha/p85 alpha) | −0.4 | 11.0 |
| PIK3CD/PIK3R1 (p110 delta/p85 alpha) | −5.8 | 9.0 |
| LIMK1 | −14.2 | −1.1 |
| LIMK2 | −3.5 | 0.4 |
| MAP3K2 (MEKK2) | 14.3 | 5.9 |
| MYLK (MLCK) | 1.6 | 1.2 |
| CDC42 BPA (MRCKA) | −1.8 | 2.8 |
| CDC42 BPB (MRCKB) | −4.6 | 3.3 |
| CDK5/p25 | 11.4 | 1.0 |
| EGFR (ErbB1) | 24.6 | −10.4 |
| EPHB1 | 19.8 | 7.1 |
| FRAP1 (mTOR) | 27.0 | 0.9 |
| IGF1R | 42.9 | −7.4 |
| MAP2K2 (MEK2) | 20.7 | 13.3 |
| MAPK3 (ERK1) | 11.5 | 6.7 |
| MAPK8 (JNK1) | −1.1 | 0.4 |
| MAPK9 (JNK2) | −8.9 | 10.9 |
| PAK1 | 24.4 | 22.7 |
| PAK2 (PAK65) | 0.3 | −8.5 |
| PAK3 | 6.3 | −10.2 |
| PAK4 | −0.2 | 6.4 |
| PAK6 | 8.9 | −0.6 |
| PAK7 (KIAA1264) | 4.9 | −11.5 |
| PDGFRA (PDGFR alpha) | 34.8 | 15.1 |
| ROCK1 | −2.0 | −4.6 |
| ROCK2 | −14.7 | −2.0 |
| SYK | 39.4 | 7.0 |
| ABL1 | 19.3 | 0.6 |
| AKT1 (PKB alpha) | −23.3 | −6.7 |
| AKT2 (PKB beta) | −22.9 | 11.5 |
| CDK1/cyclin B | 1.3 | −2.3 |
| FLT3 | 31.4 | −15.3 |
| JAK1 | 50.6 | −3.3 |
| JAK2 | 37.7 | −11.6 |
| JAK3 | 21.9 | −16.3 |
| KIT | 26.3 | −4.2 |
| SRC | 43.6 | 8.7 |

TABLE 2

GPCR Binding Assay Results

| GPCR | NSC23766 (binding percentage) | Compound 1 (binding percentage) | |
|---|---|---|---|
| B2 | −16 | 5 | Antagonist |
| CCR4 | 44 | 18 | Antagonist |
| M1 | 81 | 5 | Antagonist |
| M2 | 90 | −4 | Antagonist |
| M3 | 22 | 12 | Antagonist |
| M4 | 92 | 28 | Antagonist |
| M5 | 75 | 17 | Antagonist |
| MC5R | 20 | 0 | Antagonist |
| MTNR1A | 14 | 16 | Antagonist |
| MTNR1B | −34 | −2 | Antagonist |
| SSTR1 | −7 | −3 | Antagonist |
| SSTR5 | −11 | −6 | Antagonist |
| B2 | 4 | 2 | Agonist |
| CCR4 | 1 | 10 | Agonist |
| M1 | −9 | −4 | Agonist |
| M2 | 1 | 1 | Agonist |
| M3 | −1 | 1 | Agonist |
| M4 | 0 | 1 | Agonist |
| M5 | 0 | 0 | Agonist |
| MC5R | 10 | 0 | Agonist |
| MTNR1A | −1 | 0 | Agonist |
| MTNR1B | 3 | 4 | Agonist |
| SSTR1 | 0 | 0 | Agonist |
| SSTR5 | 2 | 0 | Agonist |

Example 9: Optimization of Lead Compound 1

SAR was performed to identify analogs of Compound that have improved properties. 56 Compounds identified in this SAR study were synthesized. Among them, 48 compounds were tested a cellular proliferation assay. Based on the test results, Compound 2 exhibited the strongest inhibition of cancer cell proliferation effect and was identified as another lead compound.

Figure 12C:
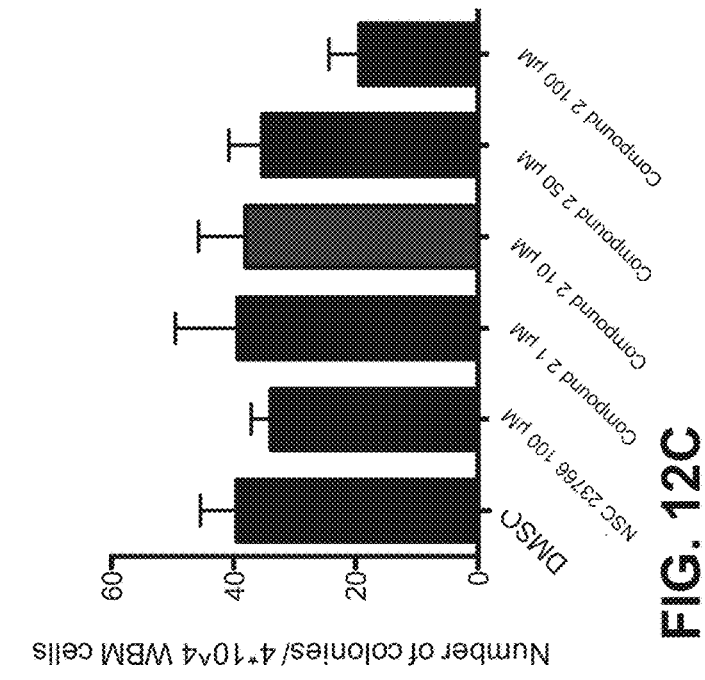
FIG. 12c shows the toxicity test results of DMSO, NSC23766, and Compound 2 in a colony forming unit assay.
Figure 12A:
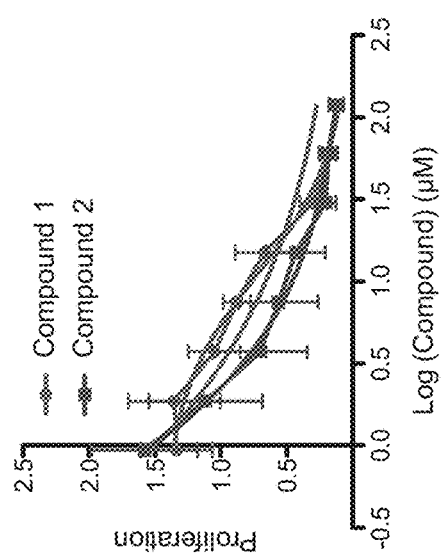
FIG. 12a shows the dose dependent inhibition of proliferation of Compound 2 in SEM cells as measured by Cell Titer Glo assay.

Example 10: Evaluation of Compound 2 of its Efficacy in Inhibiting Leukemia Cell Lines and its Toxicity Compound 2 was analyzed for its effect on cell proliferation at various doses on a SEM leukemia cell line and was compared to the effect of Compound 1 on the same cell line. The results are shown in FIG. 12a. As shown in FIG. 12a, Compound 2 exhibited improved efficacy in inhibiting proliferation of SEM cells.

Figure 12B:
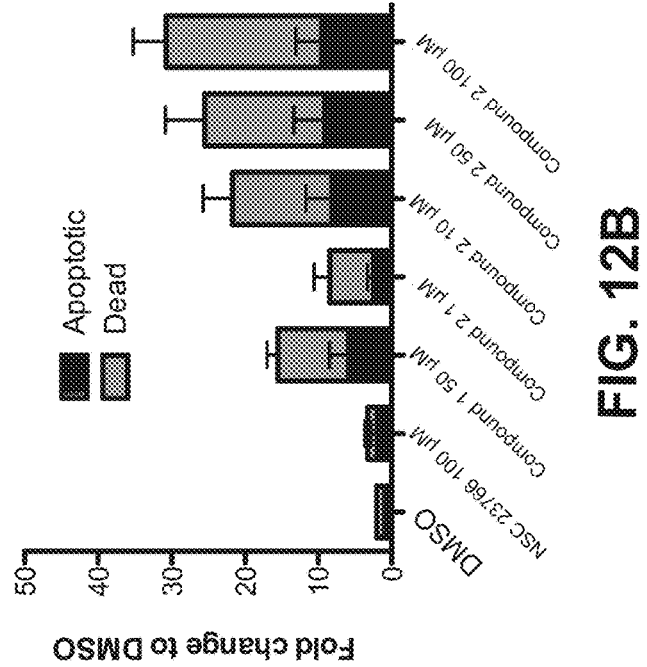
FIG. 12b shows that the effect of DMSO, NSC23766, and Compound 2 on cells apoptosis and cell death in SEM cell line.

Compound 2 was further analyzed for its effect on cell apoptosis and cell death using a flow based assay using Annexin V staining. The results are shown in FIG. 12b, which shows the effect of DMSO, NSC23766, and Compound 2 on cells apoptosis and cell death in the SEM cell line. As shown in FIG. 12b, Compound 2 caused cells apoptosis and cell death in the SEM cell line in a dose-dependent manner.

Compound 2 was also tested for toxicity in a colony forming unit assay (CFU assay), which was performed by plating normal bone marrow hematopoietic and progenitor cells in semi-solid media supplemented with different doses of Compound 2, NSC23766, and DMSO. The test results are shown in FIG. 12c. As shown in FIG. 12c, Compound 1 did not exhibit toxicity toward normal bone marrow cells.

Example 11: Evaluation of Binding Between Compound 2 and Rac1

Compound 2 was tested for its efficacy in binding with Rac1 in two independent binding assays, i.e., 2D NMR spectroscopy and Homologous time resolved fluorescence assay (HTRF).

In the 2D NMR assay, a sample containing 50 µM Rac1 and 250 µM Compound 2 was used. The NMR spectrum obtained did not indicate any significant binding of this compound to Rac1. Addition of this compound to the Tiam1-Rac complex in an HTRF binding assay didn't result in perturbation of the fluorescent emission of the proteins, suggesting no binding of the compound to the complex.

In sum, the results above suggest that Compound 2 does not substantially bind to Rac1. Without wishing to be bound by theory, it is believed that Compound 2 inhibits Rac1 activation by binding to a protein upstream of Rac1.

Example 12: In Vivo Assay for Evaluating Anti-Leukemia Activities of Compound 2

Compound 2 was evaluated for its anti-leukemia activities in mice.

Figure 13A:
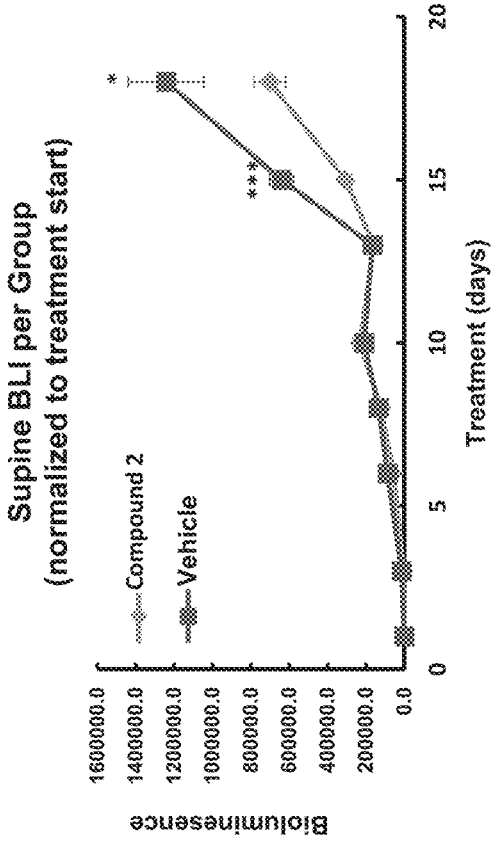
FIG. 13a shows the relative weight of the mice in the groups treated with Compound 2 and a vehicle.
Figure 13B:
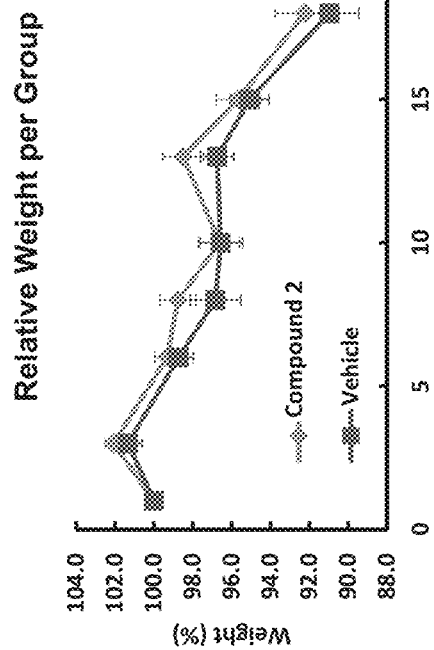
FIG. 13b shows the bioluminescence data obtained from the mice treated with Compound 2 and a vehicle when the mice were imaged in a supine position.

Specifically, cell line P12-ICHIKAWA was marked with a lentiviral vector coexpressing Luciferase and an mCherry fluorescent tag. Sorted mCherry positive P12-ICHIKAWA cells were injected into immunodeficient (NSG) mice. About 3 weeks after injection, based on an estimation of the tumor burden by quantitative assessment of bioluminescence imaging (BLI) in vivo, mice began treatment. Mice received twice daily oral doses of Compound 2 (50 mg/Kg body weight) or placebo. Each of the Compound 2 group and the vehicle group had eight mice. BLI analysis was performed three times a week to assess tumor burden. Toxicity was assessed by evaluating body weight in treated mice vs vehicle group (see FIG. 13a). The experiment was halted at day 18 after beginning of treatment due to the very aggressive nature of the disease in the vehicle group. Mice were imaged in the supine and prone position. FIG. 13b summarizes BLI values normalized to treatment start in both the compound 2 group and the vehicle group in the supine position.

Figure 13C:
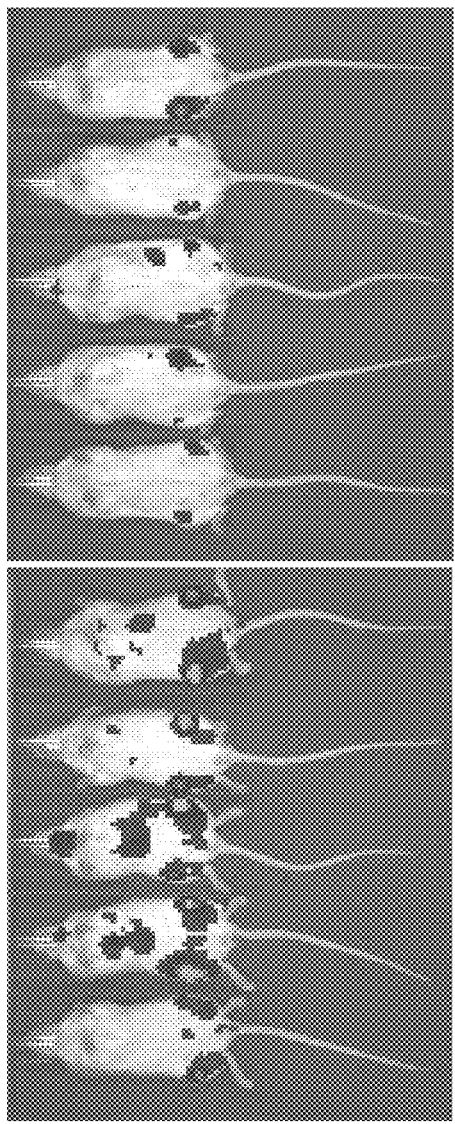
FIG. 13c shows representative actual images obtained after mice in the groups treated with Compound 2 and a vehicle for 15 days when the mice were imaged in a supine position.

As shown in these FIG. 13b, Compound 2 significantly reduced the bioluminescence in the mice when imaged in the supine position, suggesting that this compound effectively inhibited leukemia proliferation. In addition, as shown in FIG. 13a, mice in the Compound 2 group exhibited similar weight loss to those in the vehicle group, suggesting that the Compound 2 was not toxic to the mice. FIG. 13c shows representative actual images obtained after mice in the groups treated with Compound 2 and a vehicle for 15 days when the mice were imaged in a supine position.

Example 13: Evaluation of Anti-Leukemia Activities of Compound 2 in Combination with Another Anti-Cancer Compound Compound 2 was evaluated for its anti-leukemia activities in combination with each of the following three anti-cancer compounds: Dexamethasone (Dex), Vincristine (VCR), and PF-3758309 (i.e., an inhibitor of p21-activated kinases (PAKs)), which are very well characterized effectors of RAC and CDC42.

Combination experiments were carried out combining 5 doses of each drug and using a proliferation assay as a read out (ATPLite® from PerkinElmer). Drug combinations were tested on Ras-mutated P12-ICHIKAWA cells and the proliferation data were recorded 72 hours after adding the drug combinations to the culture media. Isobolograms were obtained using the CalcuSyn Software for analysis of drug interactions. The results are summarized in FIGS. 14a-14c. As shown in these three figures, all three combinations exhibited synergistic effects as the median combination index (CI) for each combination is less than 1. In particular, the combination containing Compound 2 and the PAK inhibitor PF-3758309 showed the highest synergistic effect with a median CI of 0.34.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A pharmaceutical composition, comprising a pharmaceutically acceptable carrier and a compound of formula (I) or a salt thereof:

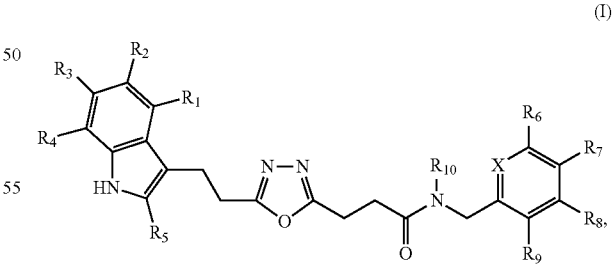

(I)

wherein
X is CH;
each of $R_1$, $R_2$, $R_3$, $R_4$, and $R_5$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_a$, $C(O)NR_aR_b$, $S(O)_2NR_aR_b$, or $NR_aR_b$;

each of $R_6$, $R_7$, $R_8$, and $R_9$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_a$, $C(O)NR_aR_b$, $S(O)_2NR_aR_b$, or $NR_aR_b$; or $R_6$ and $R_7$, or $R_8$ and $R_9$, together with the carbon atoms to which they are attached, are aryl, heteroaryl, $C_3$-$C_{20}$ cycloalkyl, or $C_1$-$C_{20}$ heterocycloalkyl;

$R_{10}$ is $C_1$-$C_{10}$ alkyl;

each $R_a$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; and each $R_b$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl.

2. The composition of claim 1, wherein each of $R_1$, $R_2$, $R_3$, $R_4$, $R_5$, $R_6$, $R_7$, $R_8$, and $R_9$, independently, is H or $C_1$-$C_{10}$ alkyl.

3. The composition of claim 2, wherein $R_7$ is $CH_2CH_3$.

4. The composition of claim 3, wherein $R_{10}$ is $CH_3$.

5. The composition of claim 1, further comprising an anti-cancer drug.

6. The composition of claim 5, wherein the anti-cancer drug is Dexamethasone, Vincristine, or a PAK inhibitor.

* * * * *

UNITED STATES PATENT AND TRADEMARK OFFICE
CERTIFICATE OF CORRECTION

PATENT NO. : 11,427,574 B2
APPLICATION NO. : 16/920016
DATED : August 30, 2022
INVENTOR(S) : Williams et al.

It is certified that error appears in the above-identified patent and that said Letters Patent is hereby corrected as shown below:

In the Claims

Column 23, Line 1, Claim 1, delete "$R_5$," and insert -- $R_8$, --.

Signed and Sealed this
Twenty-fifth Day of October, 2022

Katherine Kelly Vidal
*Director of the United States Patent and Trademark Office*